(12) United States Patent
Adams et al.

(10) Patent No.: US 11,185,324 B2
(45) Date of Patent: Nov. 30, 2021

(54) ANVIL RETENTION AND RELEASE FEATURES FOR POWERED CIRCULAR SURGICAL STAPLER

(71) Applicant: Ethicon LLC, Guaynabo, PR (US)

(72) Inventors: Shane R. Adams, Lebanon, OH (US); Thomas E. Adams, Loveland, OH (US); Nicholas J. Ross, Franklin, OH (US); Frederick E. Shelton, IV, Hillsboro, OH (US)

(73) Assignee: Cilag GmbH International, Zug (CH)

( * ) Notice: Subject to any disclaimer, the term of this patent is extended or adjusted under 35 U.S.C. 154(b) by 116 days.

(21) Appl. No.: 16/574,299

(22) Filed: Sep. 18, 2019

(65) Prior Publication Data

US 2021/0077093 A1    Mar. 18, 2021

(51) Int. Cl.
*A61B 17/068*    (2006.01)
*A61B 17/115*    (2006.01)
*A61B 17/00*    (2006.01)

(52) U.S. Cl.
CPC ...... *A61B 17/0684* (2013.01); *A61B 17/1155* (2013.01); *A61B 2017/00115* (2013.01); *A61B 2017/00137* (2013.01); *A61B 2017/00367* (2013.01); *A61B 2017/00477* (2013.01)

(58) Field of Classification Search
CPC .................. A61B 17/0684; A61B 17/1155
See application file for complete search history.

(56) References Cited

U.S. PATENT DOCUMENTS

| | | | |
|---|---|---|---|
| 5,205,459 | A | 4/1993 | Brinkerhoff et al. |
| 5,271,544 | A | 12/1993 | Fox et al. |
| 5,275,322 | A | 1/1994 | Brinkerhoff et al. |
| 5,285,945 | A | 2/1994 | Brinkerhoff et al. |
| 5,292,053 | A | 3/1994 | Bilotti et al. |

(Continued)

FOREIGN PATENT DOCUMENTS

| | | |
|---|---|---|
| EP | 3 158 949 A1 | 4/2017 |
| EP | 3 225 180 A1 | 10/2017 |

OTHER PUBLICATIONS

U.S. Appl. No. 16/574,281, entitled "Method for Controlling End Effector Closure for Powered Surgical Stapler," filed Sep. 18, 2019.

(Continued)

*Primary Examiner* — Nathaniel C Chukwurah
(74) *Attorney, Agent, or Firm* — Frost Brown Todd LLC

(57) ABSTRACT

A surgical instrument includes a body assembly, a shaft assembly extending distally from the body assembly, an anvil, and a stapling head assembly. The stapling head assembly includes at least one annular array of staples, a staple driver, and a trocar. The trocar includes a shaft defining a longitudinal axis, an actuating feature coupled with a motor unit, and at least one coupling feature. The motor unit is configured to actuate the actuating feature to move the at least one coupling feature of the trocar in a transverse direction relative to the longitudinal axis of the shaft between a contracted position and an expanded position. In the contracted position, the shaft of the trocar is configured to move along the longitudinal axis relative to the anvil. In the expanded position, the shaft of the trocar is configured to move together with the anvil along the longitudinal axis.

18 Claims, 28 Drawing Sheets

(56) References Cited

U.S. PATENT DOCUMENTS

| | | |
|---|---|---|
| 5,333,773 A | 8/1994 | Main et al. |
| 5,350,104 A | 9/1994 | Main et al. |
| 5,533,661 A | 7/1996 | Main et al. |
| 7,918,377 B2 * | 4/2011 | Measamer ......... A61B 17/1155 227/180.1 |
| 8,910,847 B2 | 12/2014 | Nalagatla et al. |
| 9,445,816 B2 | 9/2016 | Swayze et al. |
| 9,463,022 B2 | 10/2016 | Swayze et al. |
| 9,532,783 B2 | 1/2017 | Swayze et al. |
| 9,572,573 B2 | 2/2017 | Scheib et al. |
| 9,597,081 B2 | 3/2017 | Swayze et al. |
| 10,045,780 B2 | 8/2018 | Adams et al. |
| 10,058,329 B2 | 8/2018 | Gresham et al. |
| 10,307,157 B2 | 6/2019 | Miller et al. |
| 10,478,189 B2 | 11/2019 | Bear et al. |
| 2013/0175318 A1 * | 7/2013 | Felder ................ A61B 17/1155 227/175.2 |
| 2015/0083772 A1 | 3/2015 | Miller et al. |
| 2015/0083773 A1 | 3/2015 | Measamer et al. |
| 2015/0083774 A1 | 3/2015 | Measamer et al. |
| 2015/0083775 A1 | 3/2015 | Leimbach et al. |
| 2017/0258471 A1 | 9/2017 | DiNardo et al. |
| 2018/0368836 A1 | 12/2018 | Auld et al. |

OTHER PUBLICATIONS

U.S. Appl. No. 16/574,773, entitled "Method for Calibrating Movements of Actuated Members of Powered Surgical Stapler," filed Sep. 18, 2019.

U.S. Appl. No. 16/574,797, entitled "Method for Controlling Cutting Member Actuation for Powered Surgical Stapler," filed Sep. 18, 2019.

U.S. Appl. No. 62/868,457, entitled "Surgical Systems with Multiple RFID Tags," filed Jun. 28, 2019.

European Search Report and Written Opinion dated Feb. 9, 2021 for Application No. EP 20196735.3, 8 pgs.

International Search Report and Written Opinion dated Mar. 11, 2021 for Application No. PCT/IB2020/058133, 21 pgs.

* cited by examiner

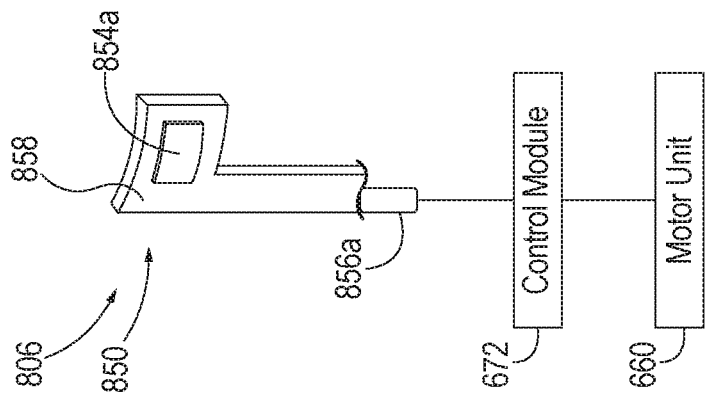
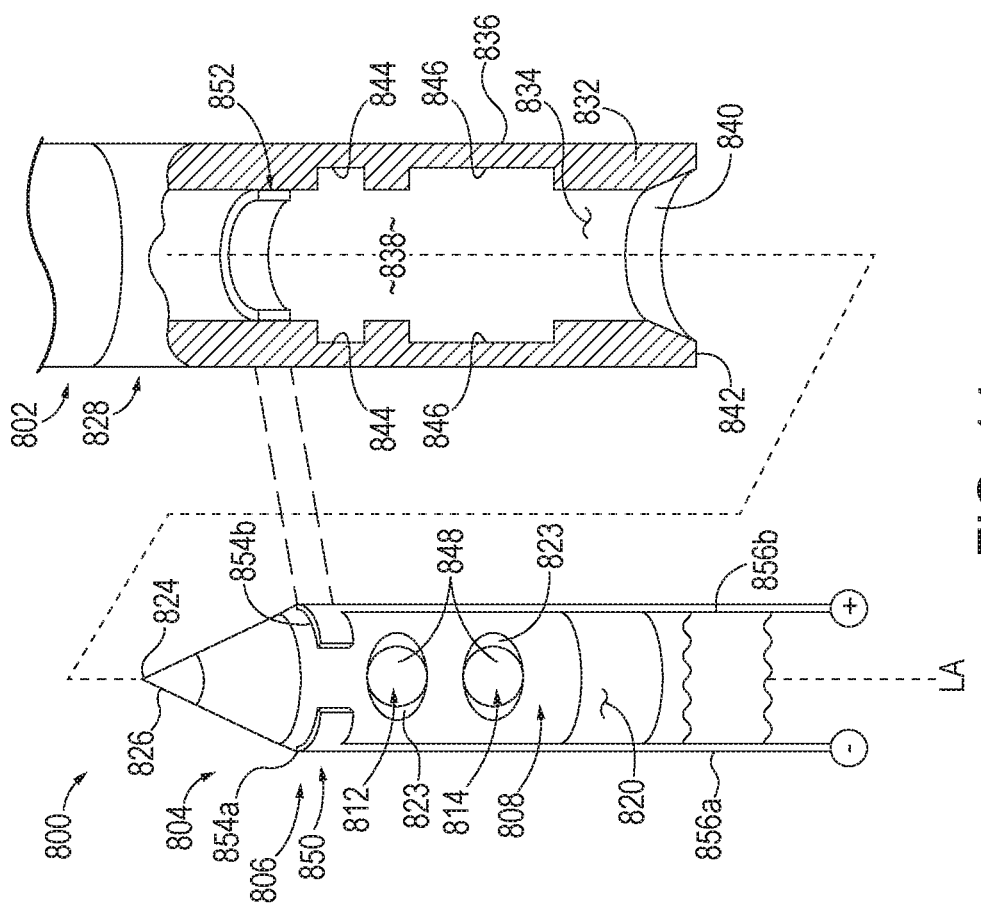
FIG. 15
FIG. 14

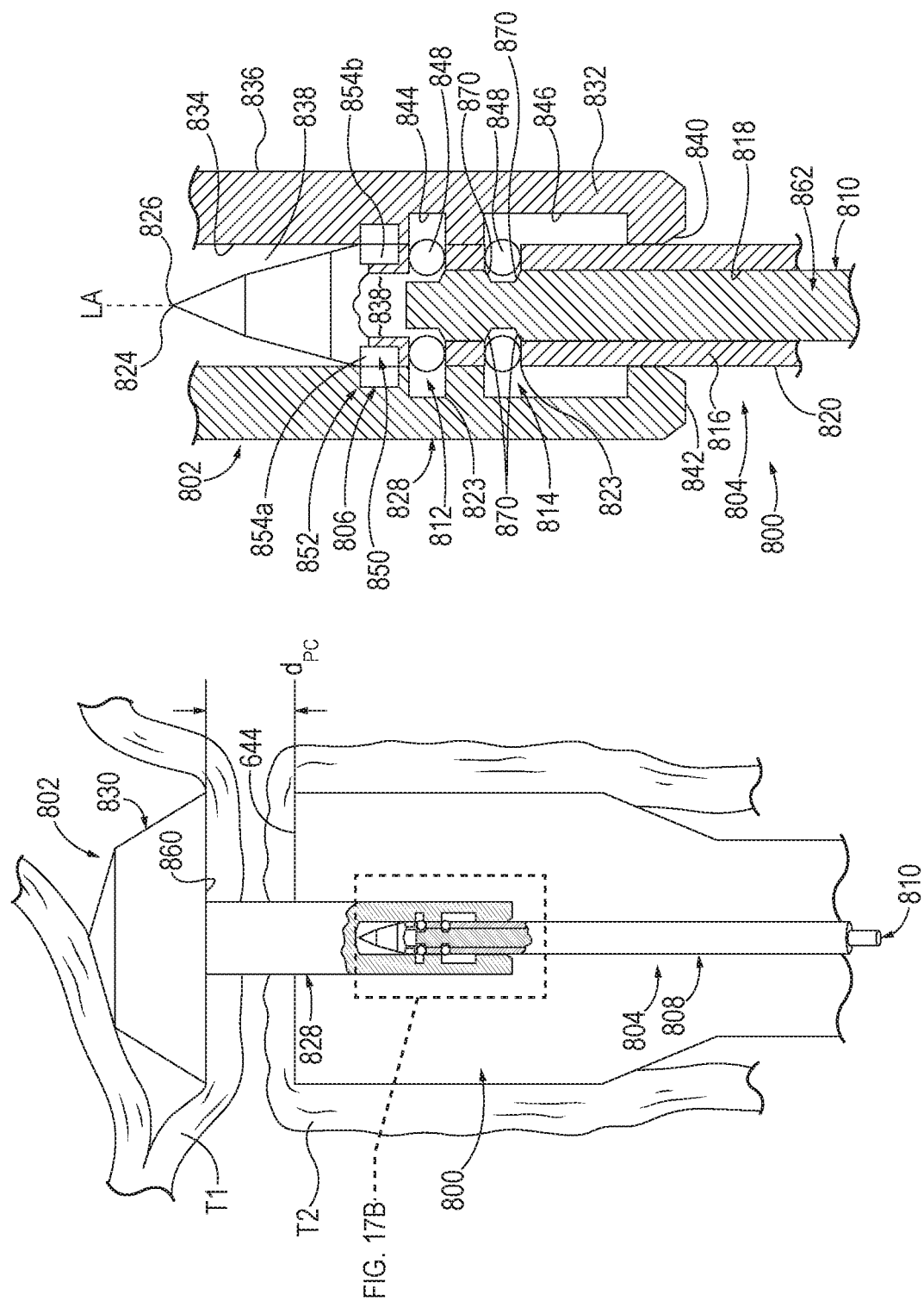

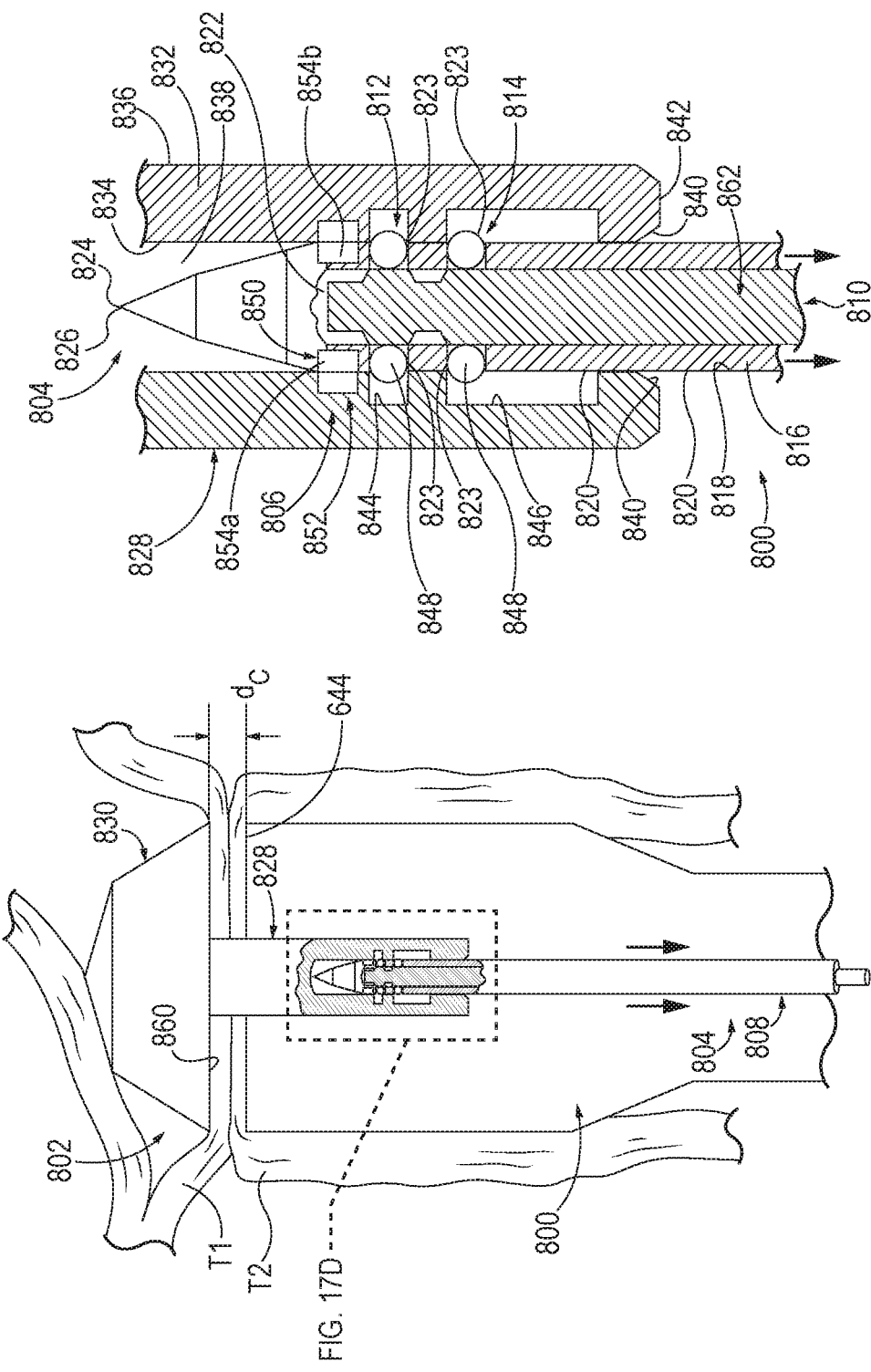

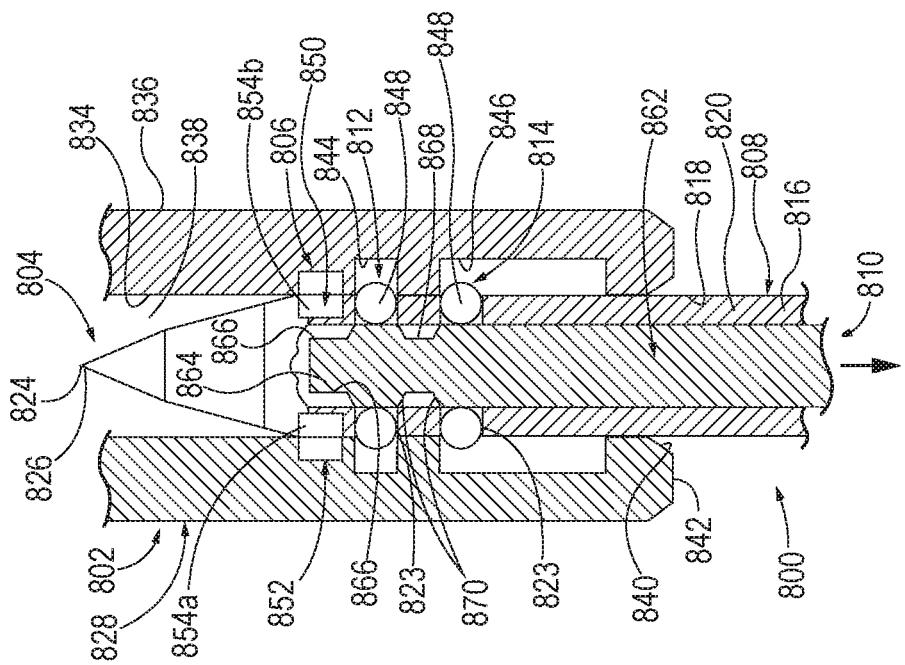
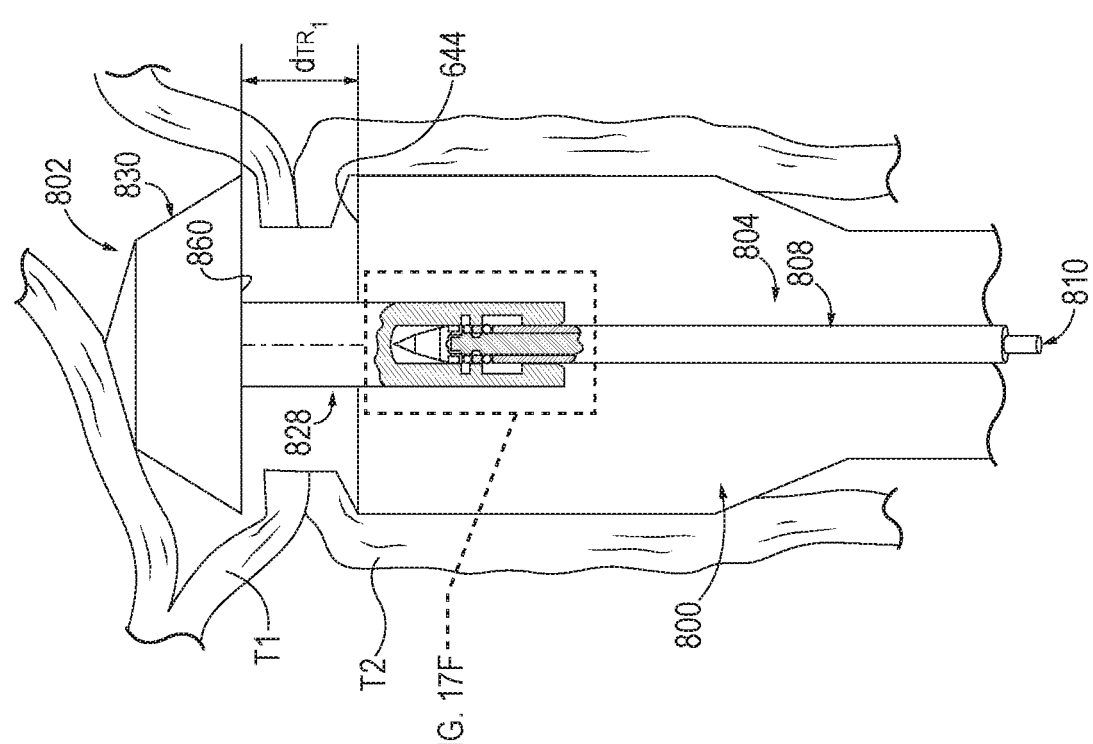
FIG. 17F
FIG. 16F

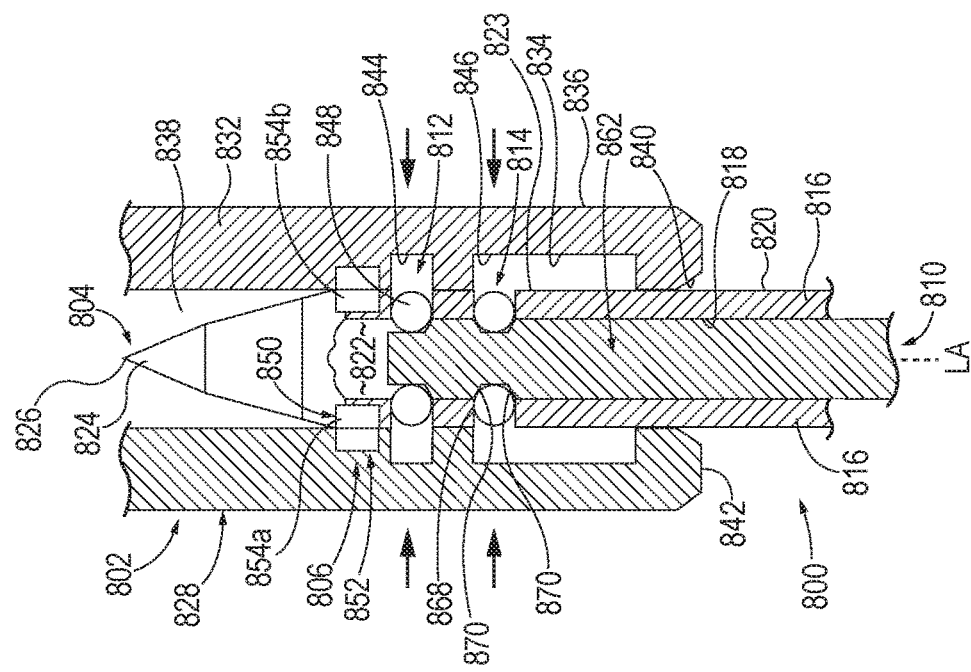
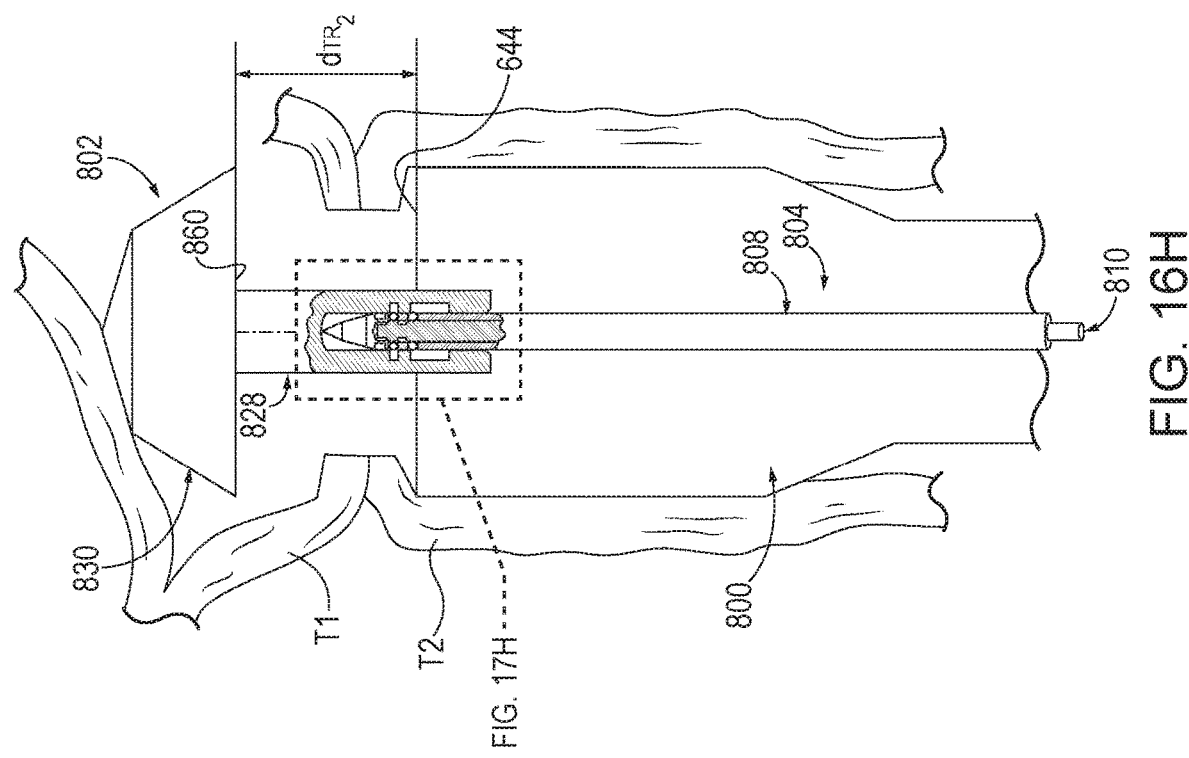

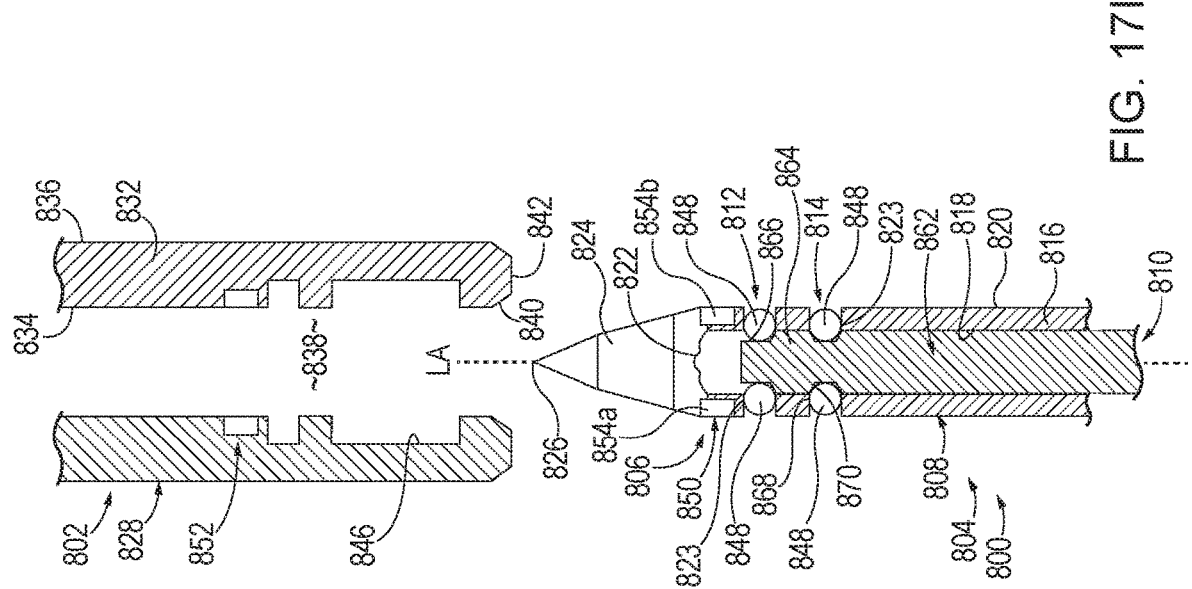
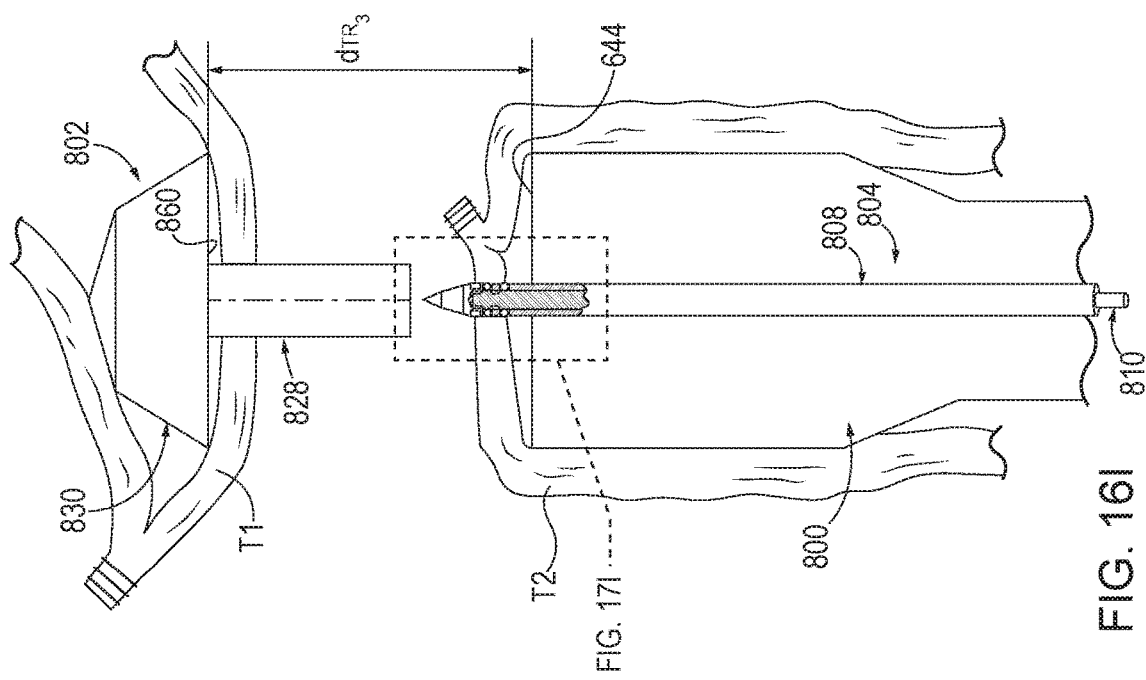

US 11,185,324 B2

ANVIL RETENTION AND RELEASE FEATURES FOR POWERED CIRCULAR SURGICAL STAPLER

BACKGROUND

In some surgical procedures (e.g., colorectal, bariatric, thoracic, etc.), portions of a patient's digestive tract (e.g., the gastrointestinal tract and/or esophagus, etc.) may be cut and removed to eliminate undesirable tissue or for other reasons. Once the tissue is removed, the remaining portions of the digestive tract may be coupled together in an end-to-end anastomosis, an end-to-side anastomosis, or a side-to-side anastomosis. The anastomosis may provide a substantially unobstructed flow path from one portion of the digestive tract to the other portion of the digestive tract, without also providing any kind of leaking at the site of the anastomosis.

One example of an instrument that may be used to provide an anastomosis is a circular stapler. Some such staplers are operable to clamp down on layers of tissue, cut through the clamped layers of tissue, and drive staples through the clamped layers of tissue to substantially seal the layers of tissue together near the severed ends of the tissue layers, thereby joining the two severed ends of the anatomical lumen together. The circular stapler may be configured to sever the tissue and seal the tissue substantially simultaneously. For instance, the circular stapler may sever excess tissue that is interior to an annular array of staples at an anastomosis, to provide a substantially smooth transition between the anatomical lumen sections that are joined at the anastomosis. Circular staplers may be used in open procedures or in endoscopic procedures. In some instances, a portion of the circular stapler is inserted through a patient's naturally occurring orifice.

Examples of circular staplers are described in U.S. Pat. No. 5,205,459, entitled "Surgical Anastomosis Stapling Instrument," issued Apr. 27, 1993; U.S. Pat. No. 5,271,544, entitled "Surgical Anastomosis Stapling Instrument," issued Dec. 21, 1993; U.S. Pat. No. 5,275,322, entitled "Surgical Anastomosis Stapling Instrument," issued Jan. 4, 1994; U.S. Pat. No. 5,285,945, entitled "Surgical Anastomosis Stapling Instrument," issued Feb. 15, 1994; U.S. Pat. No. 5,292,053, entitled "Surgical Anastomosis Stapling Instrument," issued Mar. 8, 1994; U.S. Pat. No. 5,333,773, entitled "Surgical Anastomosis Stapling Instrument," issued Aug. 2, 1994; U.S. Pat. No. 5,350,104, entitled "Surgical Anastomosis Stapling Instrument," issued Sep. 27, 1994; and U.S. Pat. No. 5,533,661, entitled "Surgical Anastomosis Stapling Instrument," issued Jul. 9, 1996; and U.S. Pat. No. 8,910,847, entitled "Low Cost Anvil Assembly for a Circular Stapler," issued Dec. 16, 2014. The disclosure of each of the above-cited U.S. Patents is incorporated by reference herein.

Some circular staplers may include a motorized actuation mechanism. Examples of circular staplers with motorized actuation mechanisms are described in U.S. Pub. No. 2015/0083772, entitled "Surgical Stapler with Rotary Cam Drive and Return," published Mar. 26, 2015, now abandoned; U.S. Pub. No. 2015/0083773, entitled "Surgical Stapling Instrument with Drive Assembly Having Toggle Features," published Mar. 26, 2015, issued as U.S. Pat. No. 9,936,949 on Apr. 10, 2018; U.S. Pub. No. 2015/0083774, entitled "Control Features for Motorized Surgical Stapling Instrument," published Mar. 26, 2015, issued as U.S. Pat. No. 9,907,552 on Mar. 6, 2018; and U.S. Pub. No. 2015/0083775, entitled "Surgical Stapler with Rotary Cam Drive," published Mar. 26, 2015, issued as U.S. Pat. No. 9,713,469 on Jul. 25, 2017. The disclosure of each of the above-cited U.S. Patent Publications is incorporated by reference herein.

While various kinds of surgical stapling instruments and associated components have been made and used, it is believed that no one prior to the inventor(s) has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 14 depicts a perspective view of an exemplary anvil and an exemplary stapling head assembly that includes a trocar and a lockout assembly;

FIG. 15 depicts a schematic view of the lockout assembly of FIG. 14;

FIG. 16B depicts a cross-sectional side view of the anvil and the trocar of the stapling head assembly of FIG. 14, with the trocar fully inserted into the anvil but with the second portion of tissue spaced from the first portion of tissue;

FIG. 16D depicts a cross-sectional side view of the anvil and the trocar of the stapling head assembly of FIG. 14, with the anvil moved proximally towards the anvil of the stapling head assembly to compress the first and second portions of tissue together to a clamped position;

FIG. 16F depicts a cross-sectional side view of the anvil and the trocar of the stapling head assembly of FIG. 14, with the trocar and the anvil distally advanced withdrawn as a unit after severing and stapling to a first tissue release position;

FIG. 16H depicts a cross-sectional side view of the anvil and the trocar of the stapling head assembly of FIG. 14, with the trocar and the anvil distally advanced withdrawn as a unit after severing and stapling to a second tissue release position;

FIG. 16I depicts a cross-sectional side view of the anvil and the trocar of the stapling head assembly of FIG. 14, with the anvil completely separated from the proximally withdrawn trocar at a third tissue release position prior to the first and second portions of tissue being severed and stapled to provide an emergency release of the anvil;

FIG. 17B depicts a detailed portion of FIG. 16B, with the trocar fully inserted into the anvil, the first and second retention features in a contracted position, and the lockout assembly in a non-locked out configuration;

FIG. 17D depicts a detailed portion of FIG. 16D, with the first and second retention features in an expanded position such that the trocar and the anvil are proximally withdrawn as a unit to the clamped position;

FIG. 17F depicts a detailed portion of FIG. 16F, with the trocar fully inserted into the anvil, the first and second retention features in an expanded position, and the actuating rod prepared to be proximally withdrawn;

FIG. 17H depicts a detailed portion of FIG. 16H, with the trocar fully inserted into the anvil, the first and second retention features in an expanded position, and the actuating rod prepared to be proximally withdrawn;

FIG. 17I depicts a detailed portion of FIG. 16I, with the anvil completely separated from the trocar;

Figure 1:
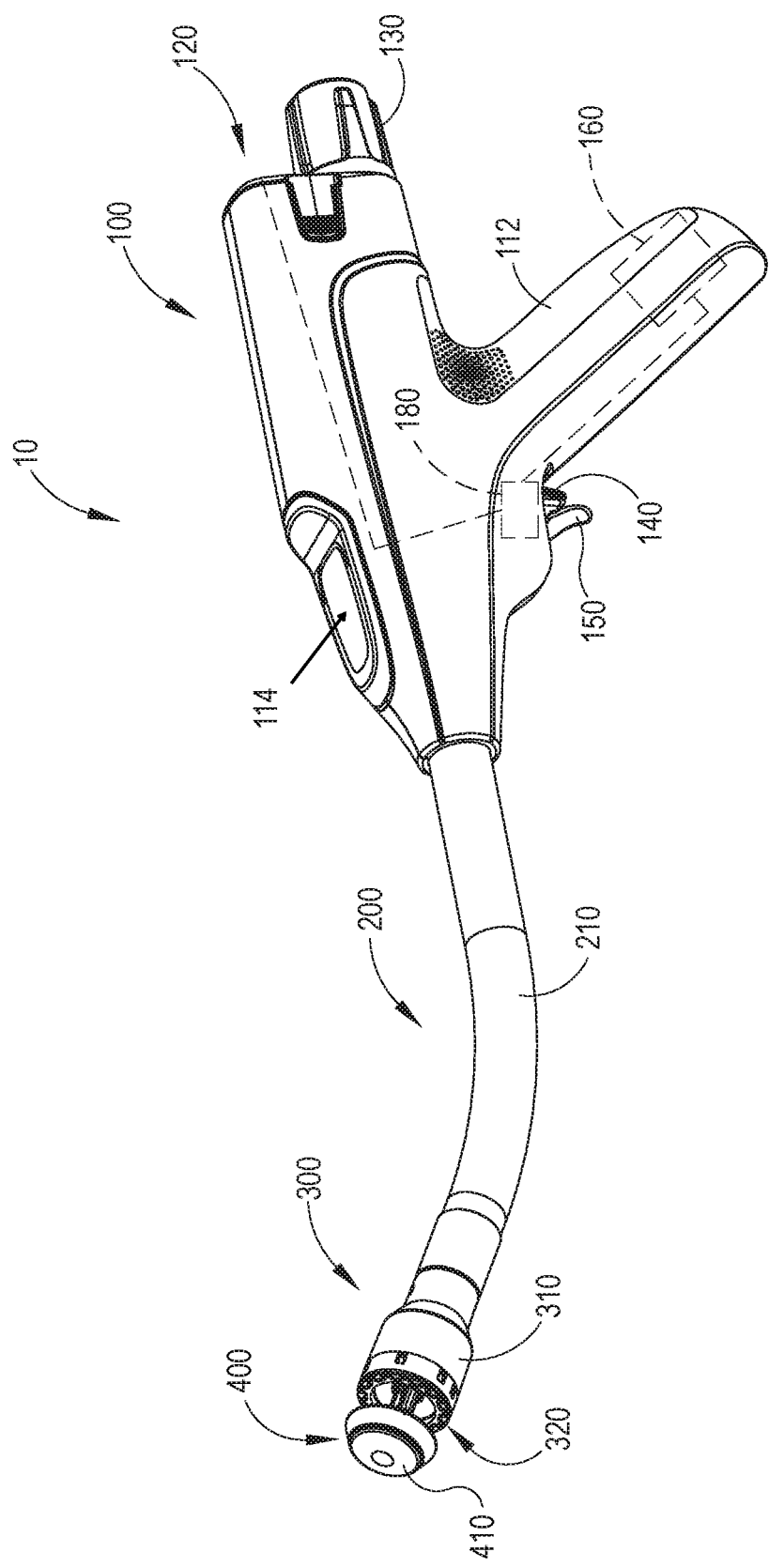
FIG. 1 depicts a perspective view of an exemplary circular surgical stapler.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

For clarity of disclosure, the terms "proximal" and "distal" are defined herein relative to a surgeon, or other operator, grasping a surgical instrument having a distal surgical end effector. The term "proximal" refers to the position of an element arranged closer to the surgeon, and the term "distal" refers to the position of an element arranged closer to the surgical end effector of the surgical instrument and further away from the surgeon. Moreover, to the extent that spatial terms such as "top," "bottom," "upper," "lower," "vertical," "horizontal," or the like are used herein with reference to the drawings, it will be appreciated that such terms are used for exemplary description purposes only and are not intended to be limiting or absolute. In that regard, it will be understood that surgical instruments such as those disclosed herein may be used in a variety of orientations and positions not limited to those shown and described herein.

I. Overview of Exemplary Circular Surgical Stapling Instrument

Figure 2:
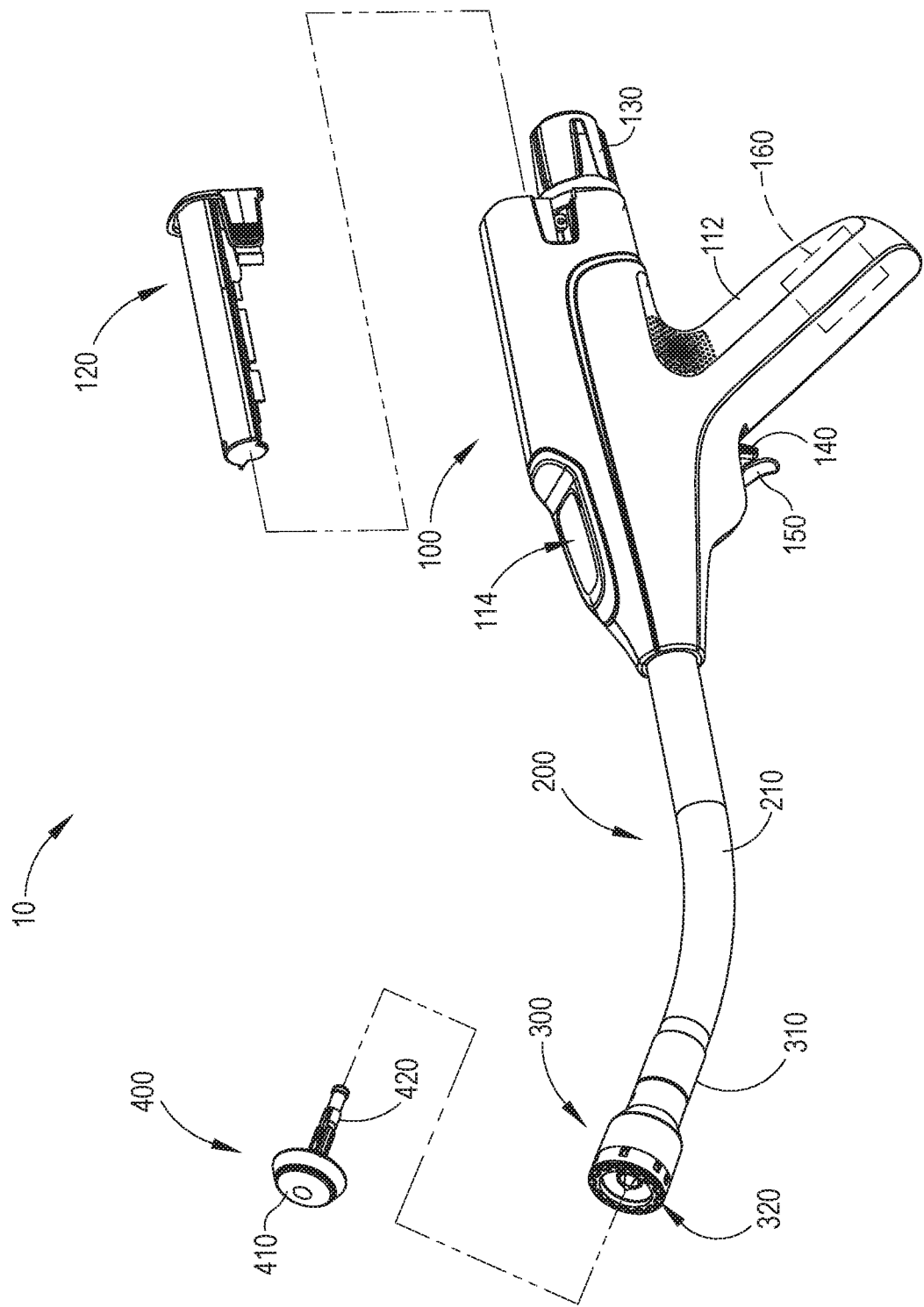
FIG. 2 depicts a perspective view of the circular stapler of FIG. 1, with a battery pack removed from a handle assembly and an anvil removed from a stapling head assembly.

FIGS. 1-2 depict an exemplary circular surgical stapling instrument (10) that may be used to provide an end-to-end, side-to-side, or end-to-side anastomosis between two sections of an anatomical lumen such as a portion of a patient's digestive tract. Instrument (10) of this example includes a body assembly (e.g. a handle assembly (100)), a shaft assembly (200) extending distally from handle assembly (100), a stapling head assembly (300) at a distal end of shaft assembly (200), and an anvil (400) configured to releasably couple and cooperate with stapling head assembly (300) to clamp, staple, and cut tissue. Instrument (10) further includes a removable battery pack (120) operable to provide electrical power to a motor (160) housed within handle assembly (100), as will be described in greater detail below.

Shaft assembly (200) extends distally from handle assembly (100) and includes a preformed bend. In some versions, the preformed bend is configured to facilitate positioning of stapling head assembly (300) within a patient's colon. Various suitable bend angles or radii that may be used will be apparent to those of ordinary skill in the art in view of the teachings herein. In some other versions, shaft assembly (200) is straight, such that shaft assembly (200) lacks a preformed bend. Various exemplary components that may be incorporated into shaft assembly (200) will be described in greater detail below.

Stapling head assembly (300) is located at the distal end of shaft assembly (200). As shown in FIGS. 1-2 and as will be described in greater detail below, anvil (400) is configured to removably couple with shaft assembly (200), adjacent to stapling head assembly (300). As will also be described in greater detail below, anvil (400) and stapling head assembly (300) are configured to cooperate to manipulate tissue in three ways, including clamping the tissue, cutting the tissue, and stapling the tissue. A knob (130) at the proximal end of handle assembly (100) is rotatable relative to casing (110) to provide precise clamping of the tissue between anvil (400) and stapling head assembly (300). When a safety trigger (140) of handle assembly (100) is pivoted away from a firing trigger (150) of handle assembly (100), firing trigger (150) may be actuated to thereby provide cutting and stapling of the tissue.

A. Exemplary Anvil

Figure 3:
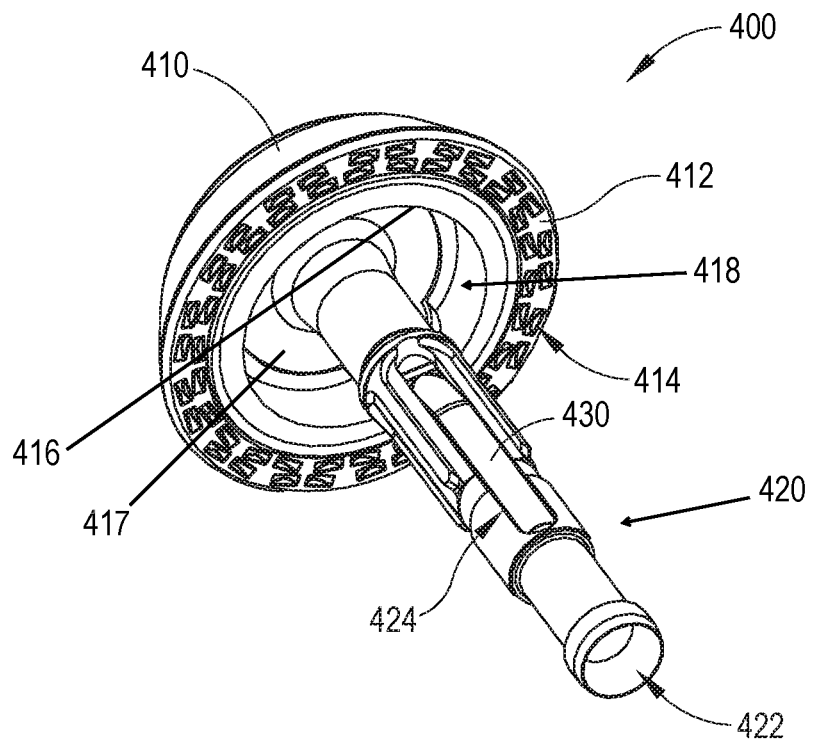
FIG. 3 depicts a perspective view of the anvil of the circular stapler of FIG. 1.

As best seen in FIG. 3, anvil (400) of the present example comprises a head (410) and a shank (420). Head (410) includes a proximal surface (412) that defines a plurality of staple forming pockets (414). Staple forming pockets (414) are arranged in two concentric annular arrays in the present example. In some other versions, staple forming pockets (414) are arranged in three or more concentric annular arrays. Staple forming pockets (414) are configured to deform staples as the staples are driven into staple forming pockets (414). For instance, each staple forming pocket (414) may deform a generally "U" shaped staple into a "B" shape as is known in the art. Proximal surface (412) terminates at an inner edge (416), which defines an outer boundary of an annular recess (418) surrounding shank (420).

Shank (420) defines a bore (422) and includes a pair of pivoting latch members (430). Latch members (430) are positioned within bore (422) such that distal ends (434) are positioned at the proximal ends of lateral openings (424), which are formed through the sidewall of shank (420). Lateral openings (424) thus provide clearance for distal ends (434) and latch shelves (436) to deflect radially outwardly from the longitudinal axis defined by shank (420). However, latch members (430) are configured to resiliently bias distal ends (434) and latch shelves (436) to pivot radially inwardly toward the longitudinal axis defined by shank (420). Latch members (430) thus act as retaining clips. This allows anvil (400) to be removably secured to an actuatable closure member in the form of a trocar (330) of stapling head assembly (300) as will be described in greater detail below. It should be understood, however, that latch members (436) are merely optional. Anvil (400) may be removably secured to trocar (330) using any other suitable components, features, or techniques.

B. Exemplary Stapling Head Assembly

Figure 4:
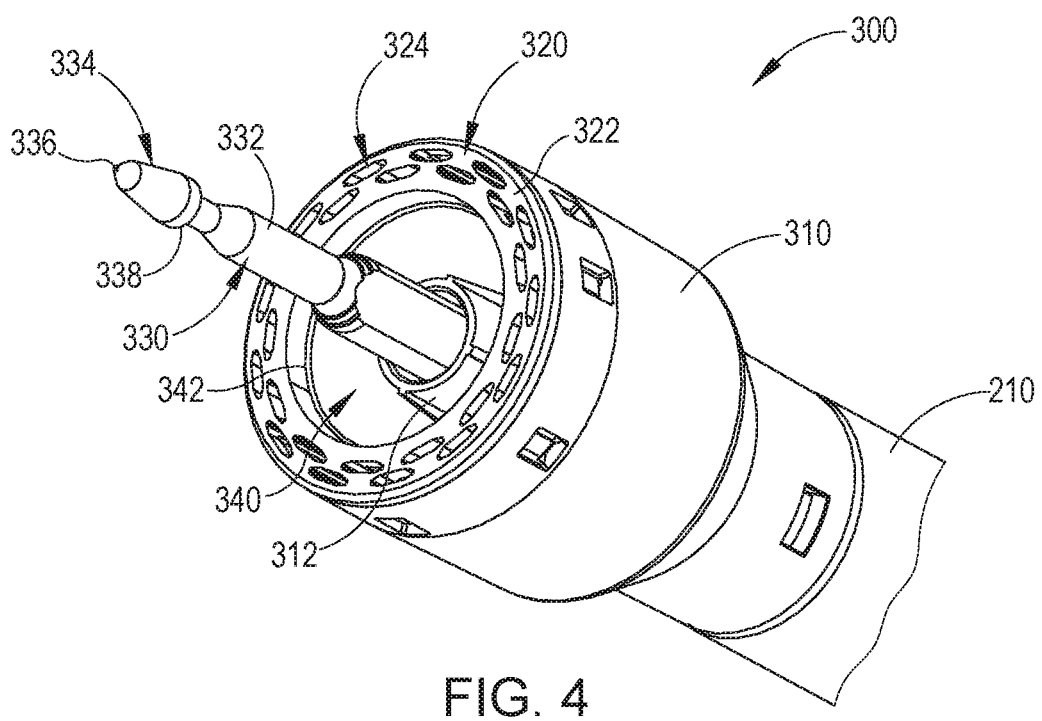
FIG. 4 depicts a perspective view of the stapling head assembly of the circular stapler of FIG. 1.
Figure 5:
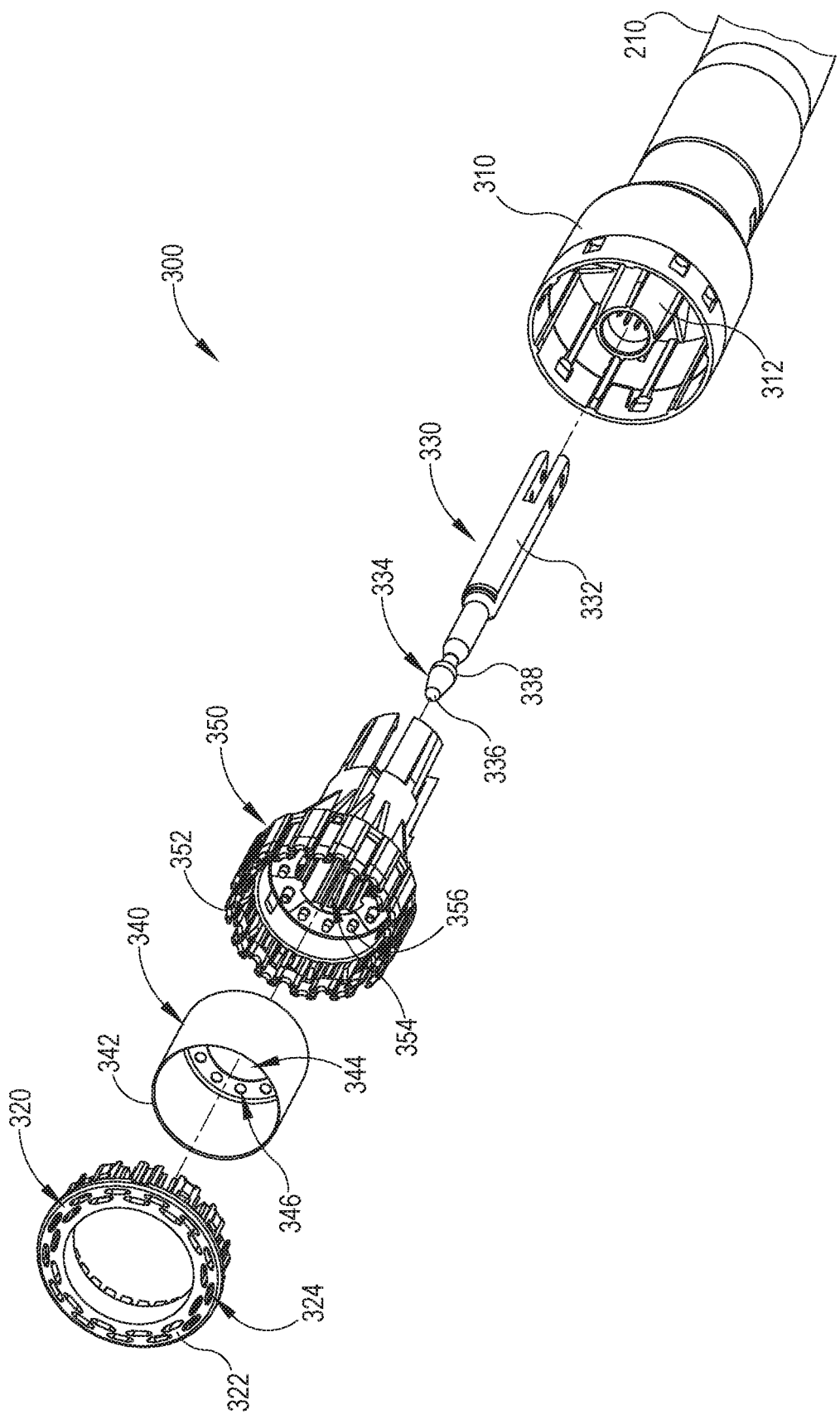
FIG. 5 depicts an exploded perspective view of the stapling head assembly of FIG. 4.

As best seen in FIGS. 4 and 5, stapling head assembly (300) of the present example is coupled to a distal end of shaft assembly (200) and comprises a body member (310) and a staple driver member (350) slidably housed therein. Body member (310) includes a distally extending cylindraceous inner core member (312). Body member (310) is fixedly secured to an outer sheath (210) of shaft assembly (200), and body member (310) and outer sheath (210) thus serve together as a mechanical ground for stapling head assembly (300). In some versions, stapling head assembly (300) may be configured to releasably couple with the distal end of shaft assembly (200), for example as disclosed in U.S. Pat. No. 9,597,081, entitled "Motor Driven Rotary Input Circular Stapler with Modular End Effector," issued Mar. 21, 2017, the disclosure of which is incorporated by reference herein.

Trocar (330) is positioned coaxially within inner core member (312) of body member (310). As will be described in greater detail below, trocar (330) is operable to translate distally and proximally relative to body member (310) in response to rotation of knob (130) relative to casing (110) of handle assembly (100). Trocar (330) comprises a shaft (332) and a head (334). Head (334) includes a pointed tip (336) and an inwardly extending proximal surface (338). Shaft (332) thus provides a reduced outer diameter just proximal to head (334), with surface (338) providing a transition between that reduced outer diameter of shaft (332) and the outer diameter of head (334). While tip (336) is pointed in the present example, tip (336) is not sharp. Tip (336) will thus not easily cause trauma to tissue due to inadvertent contact with tissue. Head (334) and the distal portion of shaft (332) are configured for insertion in bore (422) of anvil (400). Proximal surface (338) and latch shelves (436) have complementary positions and configurations such that latch shelves (436) engage proximal surface (338) when shank (420) of anvil (400) is fully seated on trocar (330). Anvil (400) is thus secured to trocar (330) through a snap fit provided by latch members (430).

Staple driver member (350) is operable to actuate longitudinally within body member (310) in response to activation of motor (160) as will be described in greater detail below. Staple driver member (350) of the present example includes two distally presented concentric annular arrays of staple drivers (352). Staple drivers (352) are arranged to correspond with the arrangement of staple forming pockets (414) of anvil (400). Thus, each staple driver (352) is configured to drive a corresponding staple into a corresponding staple forming pocket (414) when stapling head assembly (300) is actuated. It should be understood that the arrangements of staple drivers (352) and staple forming pockets (414) shown herein may be modified in any suitable manner, provided that staple drivers (352) and staple forming pockets (414) are configured to align with one another to provide proper formation of staples. Staple driver member (350) also defines a bore (354) that is configured to coaxially receive core member (312) of body member (310). An annular array of studs (356) project distally from a distally presented surface surrounding bore (354).

A cylindraceous knife member (340) is coaxially positioned within staple driver member (350). Knife member (340) includes a distally presented, sharp circular cutting edge (342). Knife member (340) is sized such that knife member (340) defines an outer diameter that is smaller than the diameter defined by the inner annular array of staple drivers (352). Knife member (340) also defines an opening that is configured to coaxially receive core member (312) of body member (310). An annular array of openings (346) formed in knife member (340) is configured to complement the annular array of studs (356) of staple driver member (350), such that knife member (340) is fixedly secured to staple driver member (350) via studs (356) and openings (346). By way of example only, studs (356) may be heat staked to knife member (340) using techniques known in the art. Other suitable structural relationships between knife member (340) and stapler driver member (350) will be apparent to those of ordinary skill in the art in view of the teachings herein.

A deck member (320) is fixedly secured to a distal end of body member (310). Deck member (320) includes a distally presented deck surface (322) defining two concentric annular arrays of staple openings (324). Staple openings (324) are arranged to correspond with the arrangement of staple drivers (352) and staple forming pockets (414) described above. Thus, each staple opening (324) is configured to provide a path for a corresponding staple driver (352) to drive a corresponding staple through deck member (320) and into a corresponding staple forming pocket (414) when stapling head assembly (300) is actuated. It should be understood that the arrangement of staple openings (324) may be modified to correspond with the arrangement of drivers (352) and staple forming pockets (414) described above. It should also be understood that various structures and techniques may be used to contain staples within stapling head assembly (300) before stapling head assembly (300) is actuated. Such structures and techniques that are used to contain staples within stapling head assembly (300) may prevent the staples from inadvertently falling out through staple openings (324) before stapling head assembly (300) is actuated. Various suitable forms that such structures and techniques may take will be apparent to those of ordinary skill in the art in view of the teachings herein.

Figure 11:
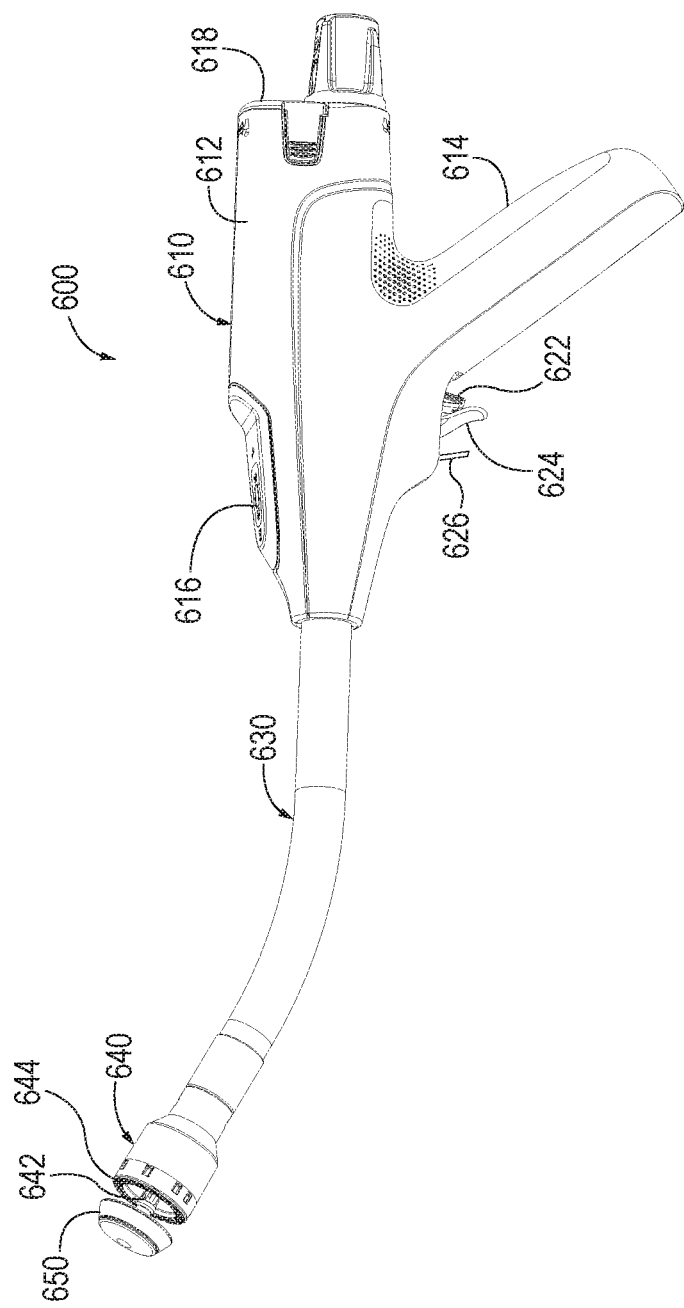
FIG. 11 depicts a perspective view of another exemplary circular surgical stapler.

As best seen in FIG. 11, deck member (320) defines an inner diameter that is just slightly larger than the outer diameter defined by knife member (340). Deck member (320) is thus configured to allow knife member (340) to translate distally to a point where cutting edge (342) is distal to deck surface (322).

In some versions of instrument (10) it may desirable to provide instrument (10) with features that are configured to indicate proper and/or improper attachment of anvil (400) to trocar (330) of stapling head assembly (300). For instance, if anvil (400) is not properly attached to trocar (330), an operator may receive audible and/or tactile feedback indicating improper attachment. Additionally, if anvil (400) is properly attached to trocar (330), an operator may receive audible, tactile, and/or visible feedback indicating proper attachment. In addition or in the alternative, features may be configured to prevent firing of stapling head assembly (300) unless anvil (400) is properly attached to trocar (330). For instance, if anvil (400) is not properly attached to trocar (330), stapling head assembly (300) may be prevented from firing. If anvil (400) is properly attached to trocar (330), firing of stapling head assembly (300) may be enabled. Such features may include various types of visual indicia, sensors, switches, and the like. By way of example only, such features may include those of the type disclosed in U.S. Pat. No. 10,307,157, entitled "Surgical Stapler with Anvil Seating Detection," issued Jun. 4, 2019, and U.S. Pub. No. 2017/0258471, entitled "Methods and Systems for Performing Circular Stapling," published Sep. 14, 2017, issued as U.S. Pat. No. 10,709,452 on Jul. 14, 2020, the disclosures of which are incorporated by reference herein.

C. Exemplary Shaft Assembly

Figure 6:
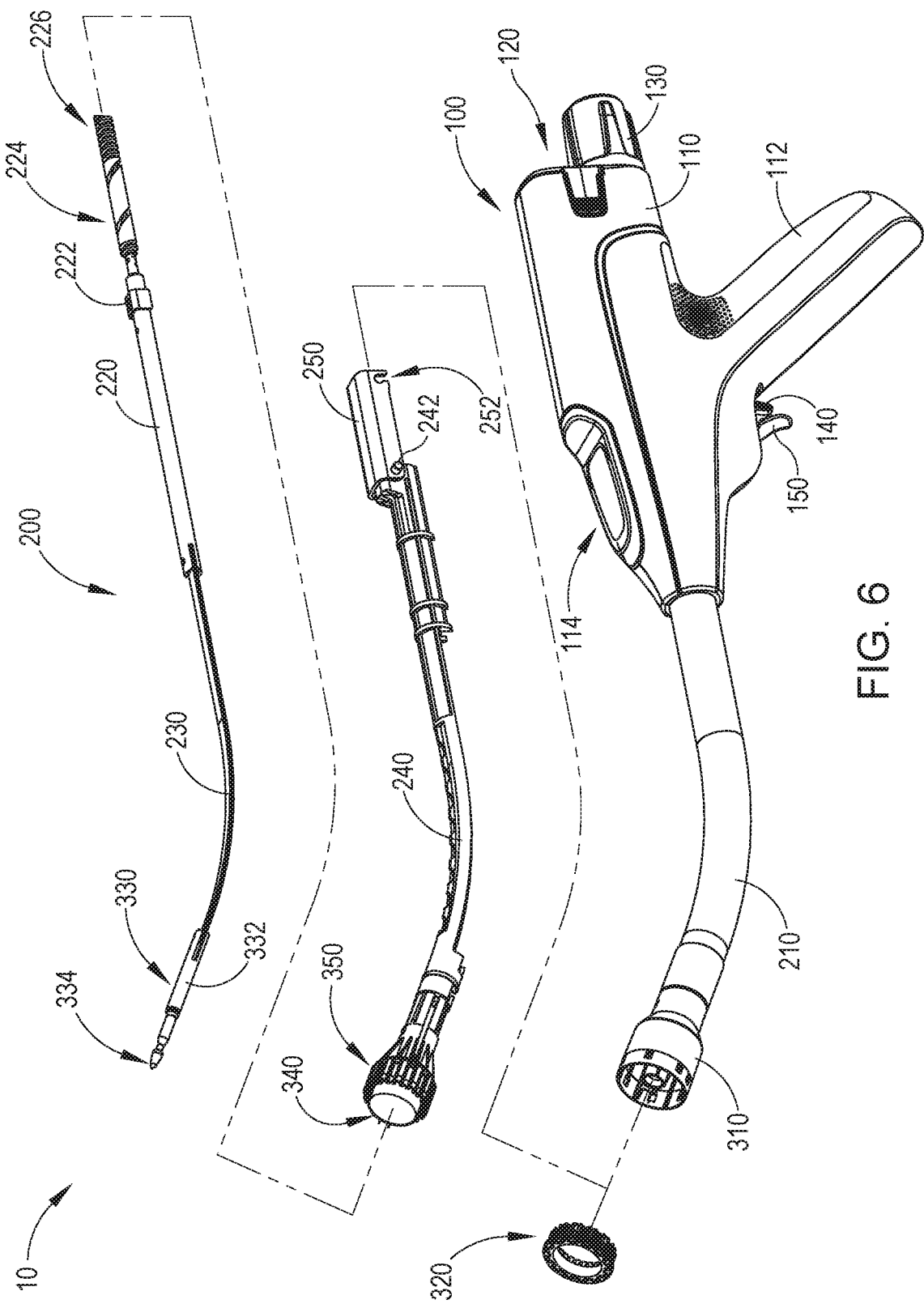
FIG. 6 depicts an exploded perspective view of the circular stapler of FIG. 1, with portions of the shaft assembly shown separated from each other.

FIG. 6 shows various components of shaft assembly (200), which couples components of stapling head assembly (300) with components of handle assembly (100). In particular, and as noted above, shaft assembly (200) includes an outer sheath (210) that extends between handle assembly (100) and body member (310). In the present example, outer sheath (210) is rigid and includes a preformed curved section as noted above.

Shaft assembly (200) further includes a trocar actuation rod (220) and a trocar actuation band assembly (230). The distal end of trocar actuation band assembly (230) is fixedly secured to the proximal end of trocar shaft (332). The proximal end of trocar actuation band assembly (230) is fixedly secured to the distal end of trocar actuation rod (220). It should therefore be understood that trocar (330) will translate longitudinally relative to outer sheath (210) in response to translation of trocar actuation band assembly (230) and trocar actuation rod (220) relative to outer sheath (210). Trocar actuation band assembly (230) is configured to flex such that trocar actuation band assembly (230) may follow along the preformed curve in shaft assembly (200) as trocar actuation band assembly (230) is translated longitudinally relative to outer sheath (210). However, trocar actuation band assembly (230) has sufficient column strength and tensile strength to transfer distal and proximal forces from trocar actuation rod (220) to trocar shaft (332). Trocar actuation rod (220) is rigid. A clip (222) is fixedly secured to trocar actuation rod (220) and is configured to cooperate with complementary features within handle assembly (100) to prevent trocar actuation rod (220) from rotating within handle assembly (100) while still permitting trocar actuation rod (220) to translate longitudinally within handle assembly (100). Trocar actuation rod (220) further includes a coarse helical threading (224) and a fine helical threading (226).

Shaft assembly (200) further includes a stapling head assembly driver (240) that is slidably received within outer sheath (210). The distal end of stapling head assembly driver (240) is fixedly secured to the proximal end of staple driver member (350). The proximal end of stapling head assembly driver (240) is secured to a drive bracket (250) via a pin (242). It should therefore be understood that staple driver member (350) will translate longitudinally relative to outer sheath (210) in response to translation of stapling head assembly driver (240) and drive bracket (250) relative to outer sheath (210). Stapling head assembly driver (240) is configured to flex such that stapling head assembly driver (240) may follow along the preformed curve in shaft assembly (200) as stapling head assembly driver (240) is translated longitudinally relative to outer sheath (210). However, stapling head assembly driver (240) has sufficient column strength to transfer distal forces from drive bracket (250) to staple driver member (350).

D. Exemplary Handle Assembly and User Input Features

As shown in FIG. 1, handle assembly (100) includes a casing (110) having a lower portion that defines an obliquely oriented pistol grip (112) and an upper portion that supports a user interface feature (114) and receives a battery pack (120), as described in greater detail below. Handle assembly (100) further includes several features that are operable to actuate anvil (400) and stapling head assembly (300). In particular, handle assembly (100) includes a rotatable knob (130), a safety trigger (140) a firing trigger (150), a motor (160), and a motor activation module (180). Knob (130) is coupled with trocar actuation rod (220) via a nut (not shown), such that coarse helical threading (224) will selectively engage a thread engagement feature within the interior of the nut; and such that fine helical threading (226) will selectively engage a thread engagement feature within the interior of knob (130). These complementary structures are configured such that trocar actuation rod (220) will first translate proximally at a relatively slow rate, then translate proximally at a relatively fast rate, in response to rotation of knob (130).

It should be understood that when anvil (400) is coupled with trocar (330), rotation of knob (130) will provide corresponding translation of anvil (400) relative to stapling head assembly (300). It should also be understood that knob (130) may be rotated in a first angular direction (e.g., clockwise) to retract anvil (400) toward stapling head assembly (300); and in a second angular direction (e.g., counterclockwise) to advance anvil (400) away from stapling head assembly (300). Knob (130) may thus be used to adjust a gap distance (d) between opposing surfaces (412, 322) of anvil (400) and stapling head assembly (300) until a suitable gap distance (d) has been achieved, for example as shown in FIG. 7C described below.

Firing trigger (150) is operable to activate motor (160) to thereby actuate stapling head assembly (300). Safety trigger (140) is operable to selectively block actuation of firing trigger (150) based on the longitudinal position of anvil (400) in relation to stapling head assembly (300). Handle assembly (100) also includes components that are operable to selectively lock out both triggers (140, 150) based on the position of anvil (400) relative to stapling head assembly (300). For instance, safety trigger (140) may be blocked from rotating from an engaged position to a disengaged position until the position of anvil (400) relative to stapling head assembly (300) is within a predefined range. Accordingly, until the anvil position is within the predefined range, actuation of firing trigger (150) is blocked by safety trigger (140), thereby inhibiting firing of stapling head assembly (300).

Firing trigger (150) of the present example includes an integral actuation paddle (not shown), which may be similar to the paddle disclosed in U.S. Pub. No. 2017/0258471, issued as U.S. Pat. No. 10,709,452 on Jul. 14, 2020, incorporated by reference above. The paddle is configured to actuate a switch of motor activation module (180) (FIG. 1) when firing trigger (150) is pivoted to a fired position. Motor activation module (180) is in communication with battery pack (120) and motor (160), such that motor activation module (180) is configured to provide activation of motor (160) with electrical power from battery pack (120) in response to the paddle actuating the switch of motor activation module (180). Thus, motor (160) will be activated when firing trigger (150) is pivoted. This activation of motor (160) will actuate stapling head assembly (300) via drive bracket (250), as described in greater detail below. Though not shown, and by way of example only, motor (160) may be operatively coupled with drive bracket (250) via a gearbox coupled with an output shaft of motor (160), a rotary cam member coupled with an output shaft of the gearbox, and a cam follower coupled with the rotary cam member, for example as disclosed in U.S. Pub. No. 2017/0258471, issued as U.S. Pat. No. 10,709,452 on Jul. 14, 2020, incorporated by reference above.

As best shown in FIGS. 1-2, handle assembly (100) is further configured to releasably receive a battery pack (120) operable to provide electrical power to motor (160), as noted above. It should be understood that battery pack (120) and handle assembly (100) may have complementary electrical contacts, pins and sockets, and/or other features that provide paths for electrical communication from battery pack (120) to electrically powered components in handle assembly (100) when battery pack (120) is coupled with handle assembly (100). It should also be understood that, in some versions, battery pack (120) may be unitarily integrated within handle assembly (100) such that battery back (120) cannot be removed from handle assembly (100).

E. Exemplary Anastomosis Procedure with Circular Stapling Instrument

FIGS. 7A-7E show instrument (10) being used to form an anastomosis (70) between two tubular anatomical structures (20, 40). By way of example only, the tubular anatomical structures (20, 40) may comprise sections of a patient's esophagus, sections of a patient's colon, other sections of the patient's digestive tract, or any other tubular anatomical structures. In some versions, one or more diseased portions of a patient's colon are removed, with the tubular anatomical structures (20, 40) of FIGS. 7A-7E representing the remaining severed portions of the colon.

Figure 7A:
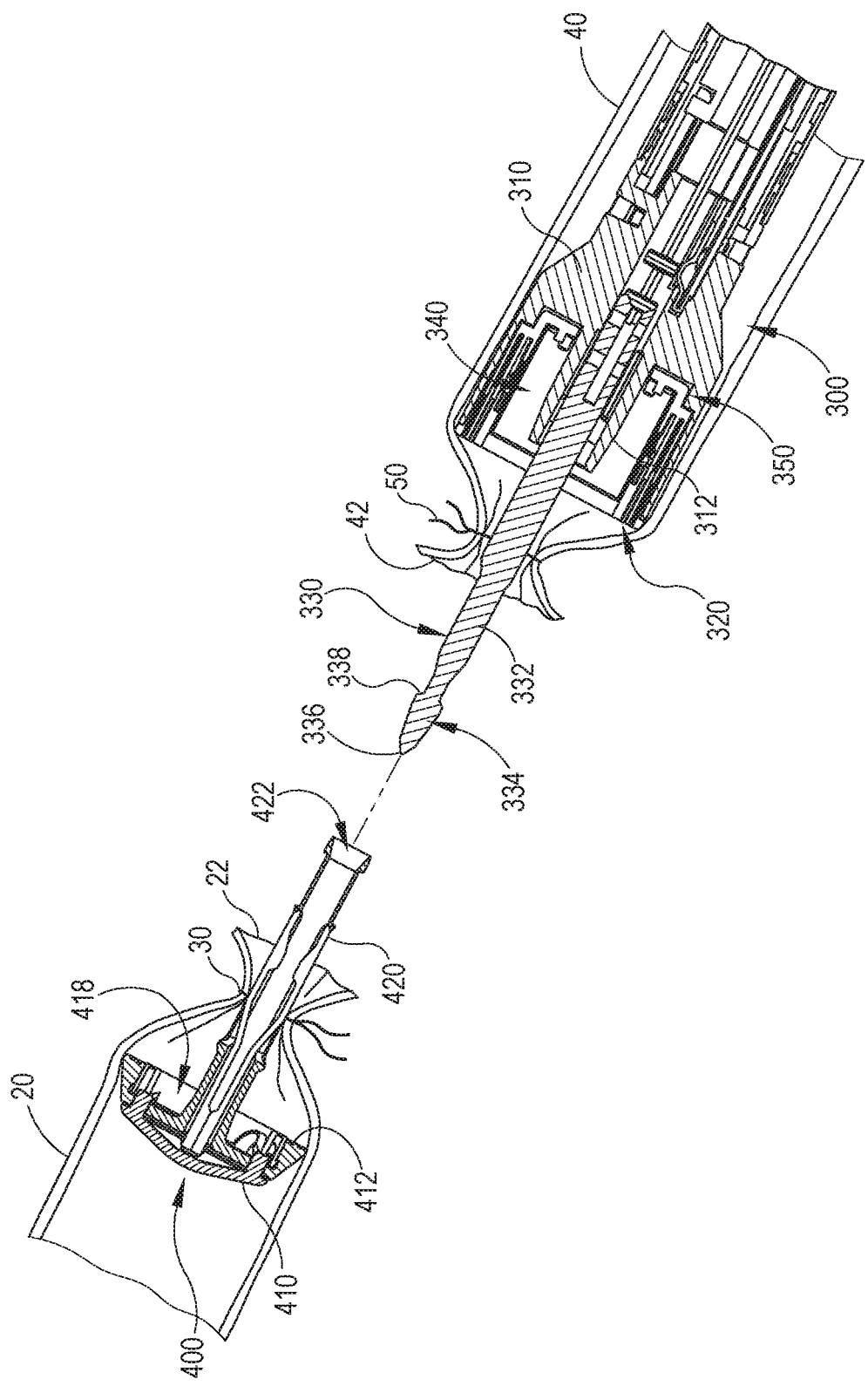
FIG. 7A depicts a cross-sectional side view of the anvil of FIG. 3 positioned within a first section of a digestive tract and the stapling head assembly of FIG. 4 positioned in a second section of the digestive tract, with the anvil separated from the stapling head assembly.

As shown in FIG. 7A, anvil (400) is positioned in one tubular anatomical structure (20) and stapling head assembly (300) is positioned in another tubular anatomical structure (40). In versions where tubular anatomical structures (20, 40) comprise sections of a patient's colon, stapling head assembly (300) may be inserted via the patient's rectum. It should also be understood that the procedure depicted in FIGS. 7A-7E is an open surgical procedure, though the procedure may instead be performed laparoscopically. Various suitable ways in which instrument (10) may be used to form an anastomosis (70) in a laparoscopic procedure will be apparent to those of ordinary skill in the art in view of the teachings herein.

As shown in FIG. 7A, anvil (400) is positioned in tubular anatomical structure (20) such that shank (420) protrudes from the open severed end (22) of tubular anatomical structure (20). In the present example, purse-string suture (30) is provided about a mid-region of shank (420) to generally secure the position of anvil (400) in tubular anatomical structure (20). In some other variations, purse-string suture (30) is tightened around the proximal end of shank (420). In some such variations, the proximal end of shank (420) may include a notch or other feature to securely capture purse-string suture (30). Continuing with the present example, stapling head assembly (300) is positioned in tubular anatomical structure (40) such that trocar (330) protrudes from the open severed end (42) of tubular anatomical structure (20). A purse-string suture (50) is provided about a mid-region of shaft (332) to generally secure the position of stapling head assembly (300) in tubular anatomical structure (40). Stapling head assembly (300) is then urged distally to ensure that stapling head assembly (300) is fully seated at the distal end of tubular anatomical structure (40).

Figure 7B:
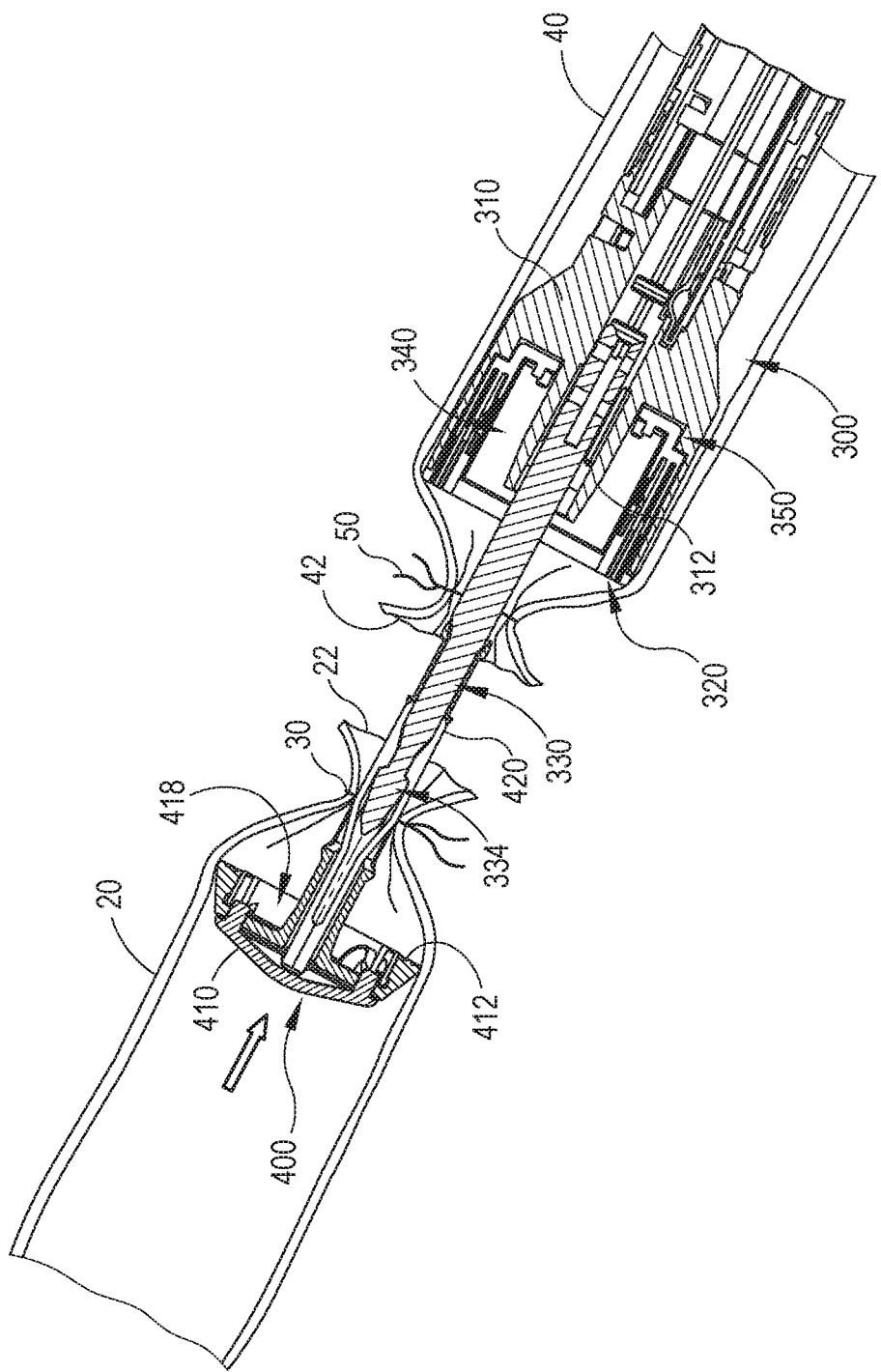
FIG. 7B depicts a cross-sectional side view of the anvil of FIG. 3 positioned within the first section of the digestive tract and the stapling head assembly of FIG. 4 positioned in the second section of the digestive tract, with the anvil secured to the stapling head assembly.
Figure 7C:
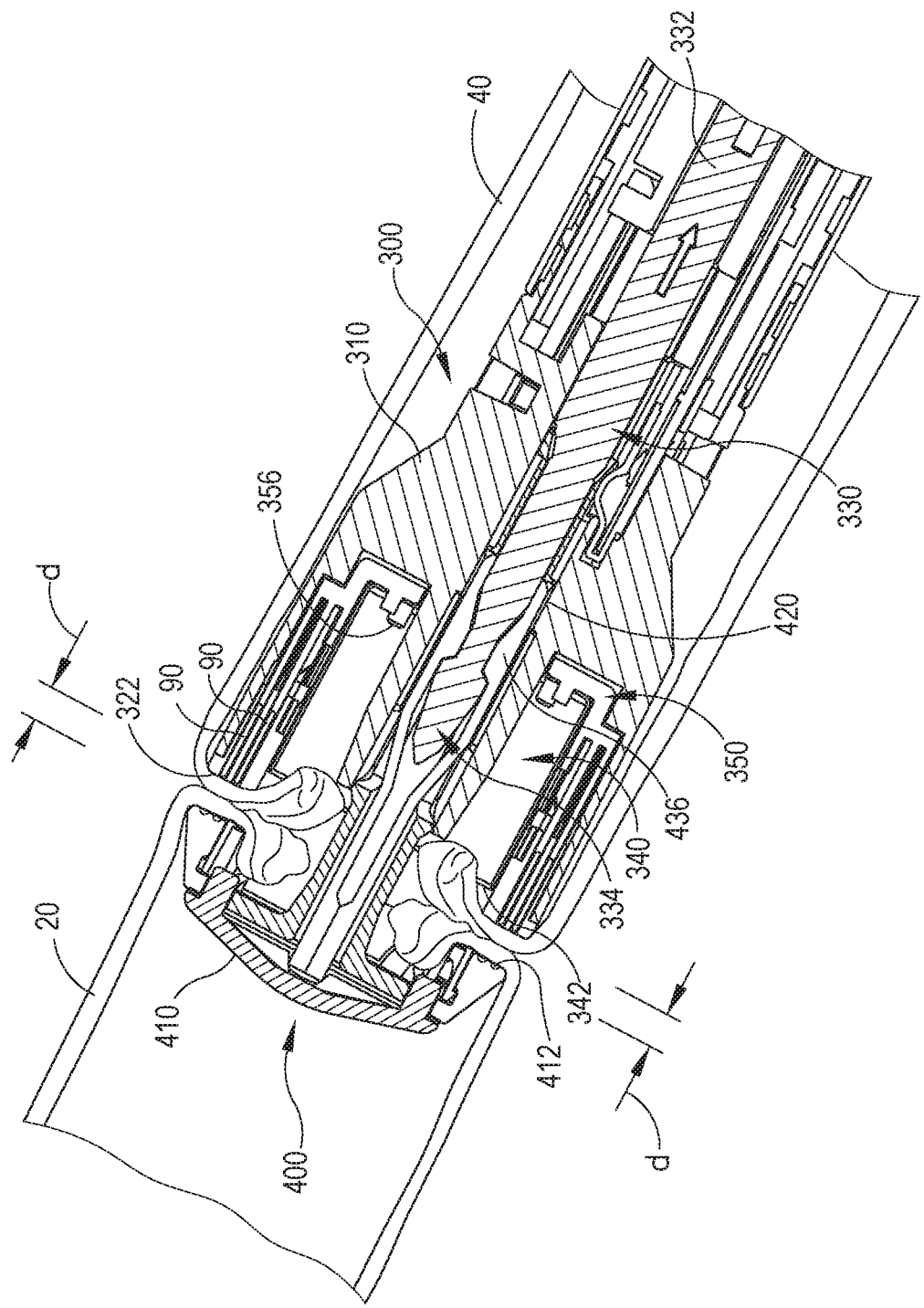
FIG. 7C depicts a cross-sectional side view of the anvil of FIG. 3 positioned within the first section of the digestive tract and the stapling head assembly of FIG. 4 positioned in the second section of the digestive tract, with the anvil retracted toward the stapling head assembly to thereby clamp tissue between the anvil and the stapling head assembly.

Next, anvil (400) is secured to trocar (330) by inserting trocar (330) into bore (422) as shown in FIG. 7B. Latch members (430) engage head (334) of trocar (330), thereby providing a secure fit between anvil (400) and trocar (330). The operator then rotates knob (130) while holding casing (110) stationary via pistol grip (112). This rotation of knob (130) causes trocar (330) and anvil (400) to retract proximally. As shown in FIG. 7C, this proximal retraction of trocar (330) and anvil (400) compresses the tissue of tubular anatomical structures (20, 40) between surfaces (412, 322) of anvil (400) and stapling head assembly (300). As this occurs, the operator may observe the tactile resistance or feedback via knob (130) while turning knob (130), with such tactile resistance or feedback indicating that the tissue is being compressed. As the tissue is being compressed, the operator may visually observe the position of an indicator needle (522) within a user interface feature (114) of handle assembly (100) to determine whether the gap distance (d) between opposing surfaces (412, 322) of anvil (400) and stapling head assembly (300) is appropriate; and make any necessary adjustments via knob (130).

Figure 7D:
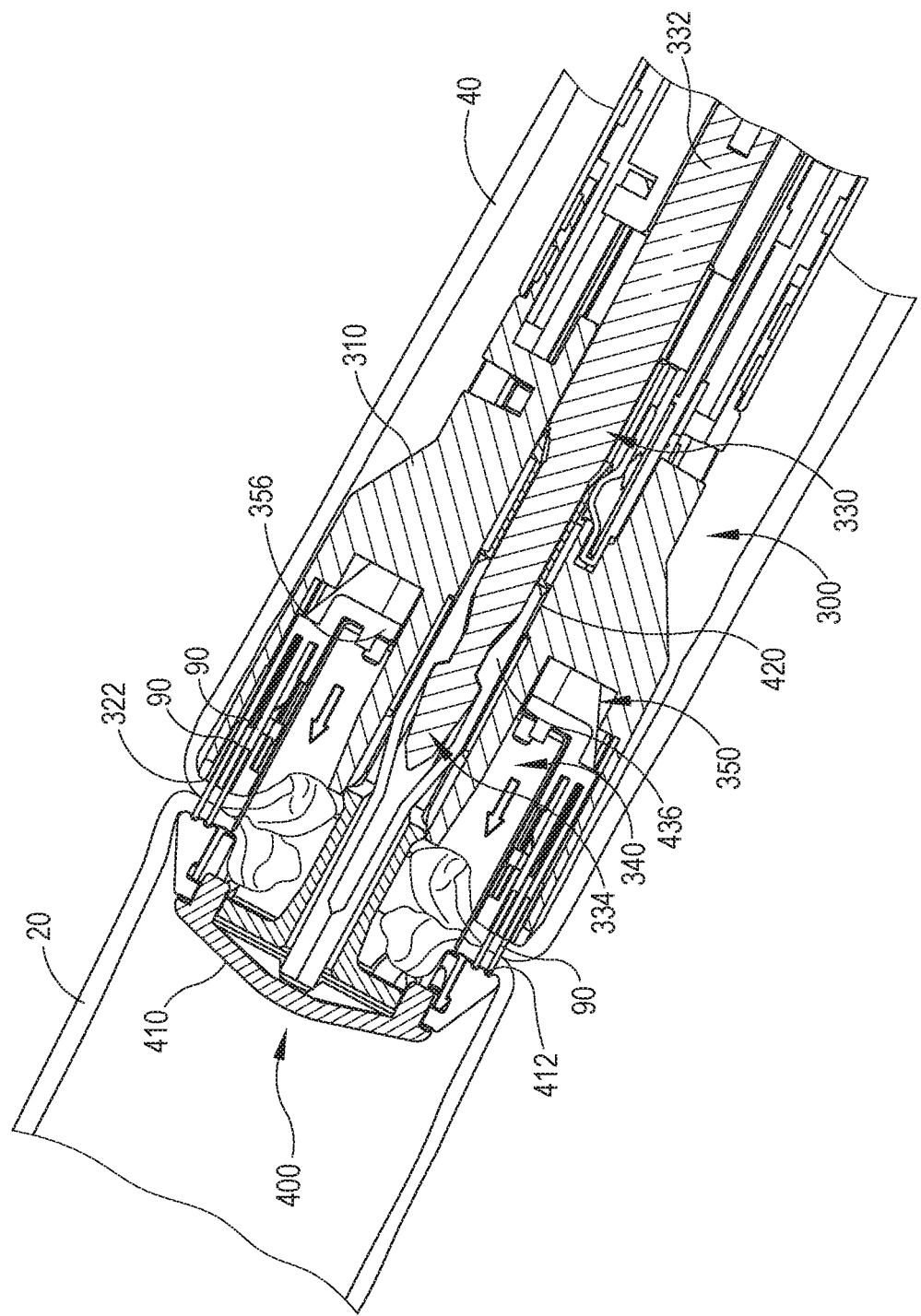
FIG. 7D depicts a cross-sectional side view of the anvil of FIG. 3 positioned within the first section of the digestive tract and the stapling head assembly of FIG. 4 positioned in the second section of the digestive tract, with the stapling head assembly actuated to sever and staple the clamped tissue.

Once the operator has appropriately set the gap distance (d) via knob (130), the operator pivots safety trigger (140) toward pistol grip (112) to enable actuation of firing trigger (150). The operator then pivots firing trigger (150) toward pistol grip (112), thus causing paddle (158) to actuate the switch of motor activation module (180) and thereby activate motor (160) to rotate. This rotation of motor (160) causes actuation (or "firing") of stapling head assembly (300) by actuating drive bracket (250) distally to thereby drive knife member (340) and staple driver member (350) distally, as shown in FIG. 7D. As knife member (340) translates distally, cutting edge (342) of knife member (340) cuts excess tissue that is positioned within annular recess (418) of anvil (400) and the interior of knife member (340).

As shown in FIG. 3, anvil (400) of the present example includes a breakable washer (417) positioned within annular recess (418). This washer (417) is broken by knife member (340) when the knife member (340) completes a full distal range of motion from the position shown in FIG. 7C to the position shown in FIG. 7D. Features of stapler (10) may be configured to provide an increasing mechanical advantage as knife member (340) reaches the end of its distal movement, thereby providing greater force by which to break the washer (417). Of course, the breakable washer (417) may be omitted entirely in some versions. In versions where washer (417) is included, it should be understood that washer (417) may also serve as a cutting board for knife member (340) to assist in cutting of tissue.

As staple driver member (350) translates distally from the position shown in FIG. 7C to the position shown in FIG. 7D, staple driver member (350) drives staples (90) through the tissue of tubular anatomical structures (20, 40) and into staple forming pockets (414) of anvil (400). Staple forming pockets (414) deform the driven staples (90) into a "B" shape or a three-dimensional shape, for example, such that the formed staples (90) secure the ends of tissue together, thereby coupling tubular anatomical structure (20) with tubular anatomical structure (40).

Figure 7E:
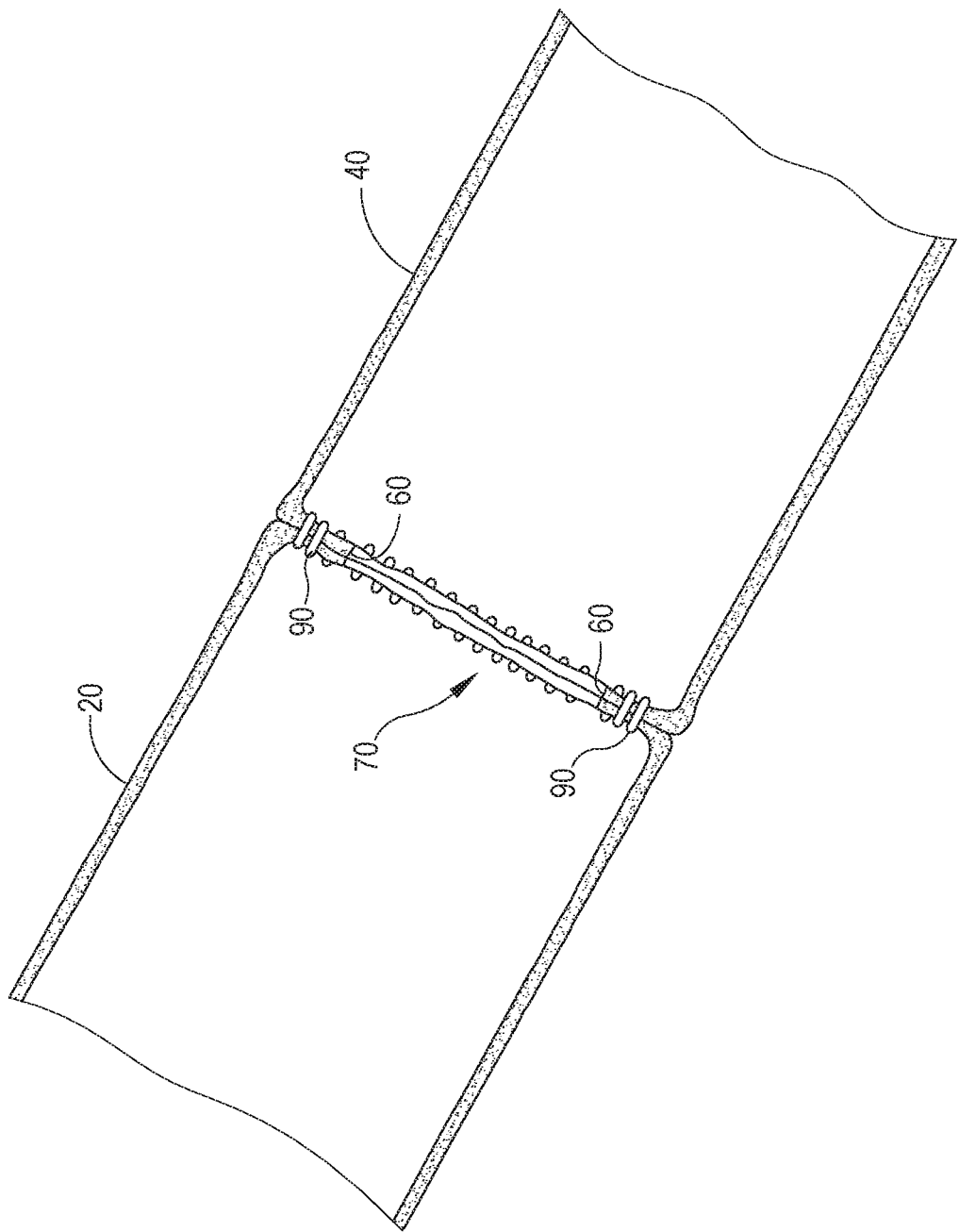
FIG. 7E depicts a cross-sectional side view of the first and second sections of the digestive tract of FIG. 7A joined together at an end-to-end anastomosis.

After the operator has actuated stapling head assembly (300) as shown in FIG. 7D, the operator rotates knob (130) to drive anvil (400) distally away from stapling head assembly (300), increasing the gap distance (d) to facilitate release of the tissue between surfaces (412, 322). The operator then removes instrument (10) from the patient, with anvil (400) still secured to trocar (330). Referring back to the example where the tubular anatomical structures (20, 40) comprise sections of a patient's colon, instrument (10) may be removed via the patient's rectum. With instrument (10) removed, the tubular anatomical structures (20, 40) are left secured together by two annular arrays of staples (90) at an anastomosis (70) as shown in FIG. 7E. The inner diameter of the anastomosis (70) is defined by the severed edge (60) left by knife member (340).

F. Exemplary Trocar with Integral Circuit

Figure 8:
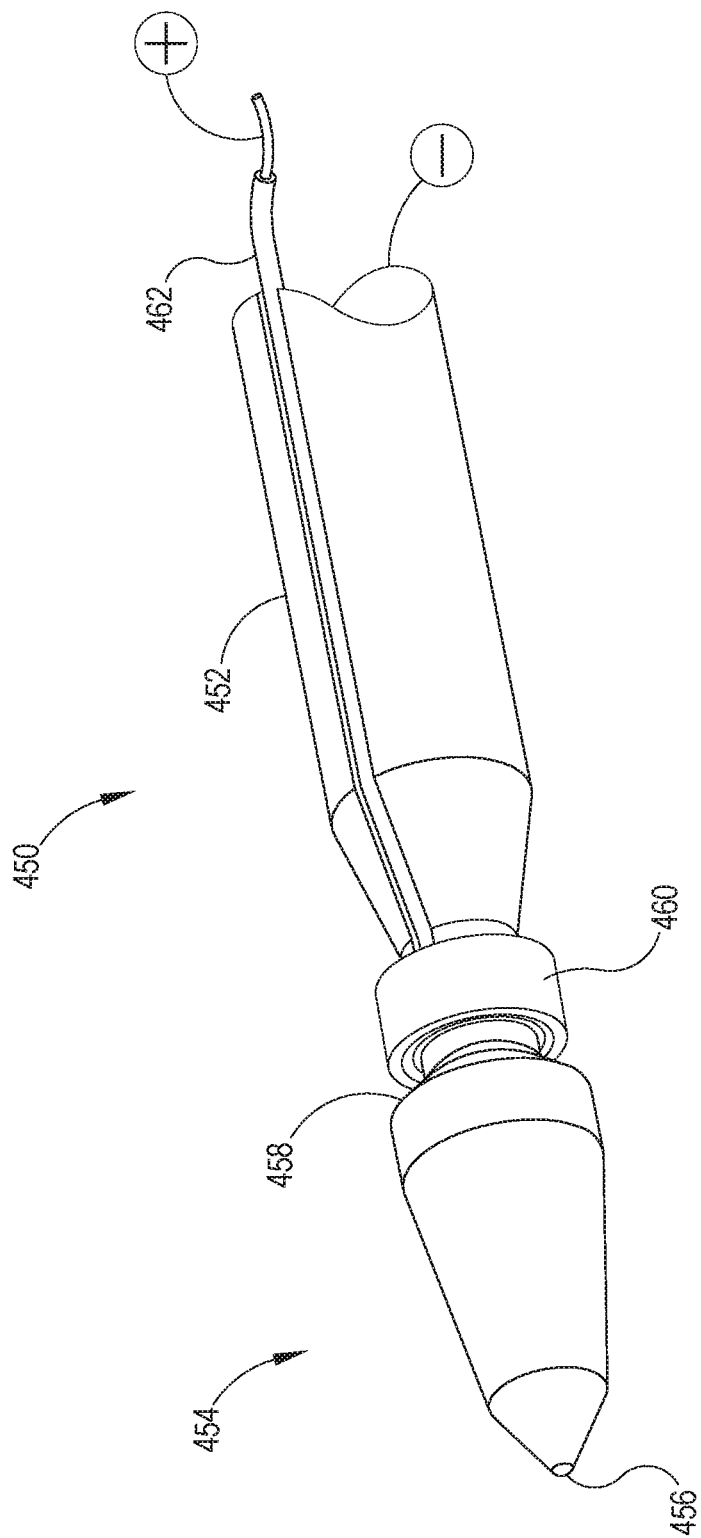
FIG. 8 depicts a perspective view of the distal end of another exemplary alternative trocar.
Figure 9A:
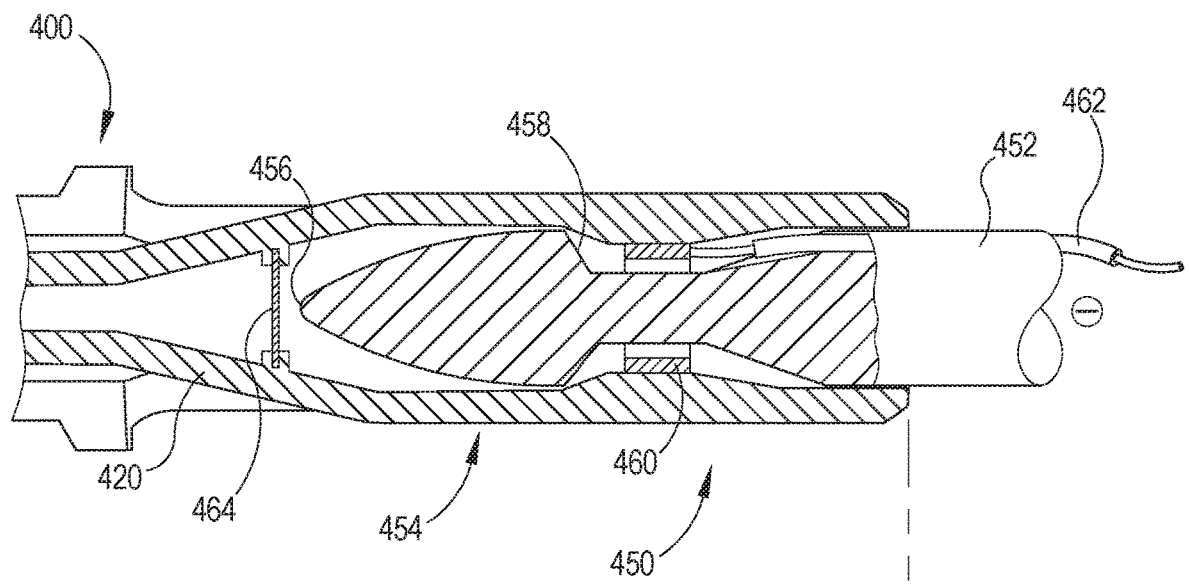
FIG. 9A depicts a cross-sectional side view of the distal end of the trocar of FIG. 8, with a circuit of the trocar in an open state.

FIGS. 8-9A depict an exemplary trocar (450) that may be readily incorporated into instrument (10) discussed above in place of trocar (330). Trocar (450) of this example is configured to operate substantially similar to trocar (330) discussed above except for the differences discussed below. For instance, trocar (450) is operable to translate distally in response to rotation of knob (130). As will be discussed in more detail below, anvil (400) is configured to be attached to trocar (450) such that translation of trocar (450) is communicated directly to anvil (400).

Trocar (450) comprises a shaft (452) and a head (454). Head (454) includes a pointed tip (456) and an inwardly extending proximal surface (458). Shaft (452) thus provides a reduced outer diameter just proximal to head (454), with surface (458) providing a transition between that reduced outer diameter of shaft (452) and the outer diameter of head (454). While tip (456) is pointed in the present example, tip (456) is not sharp. Tip (456) will thus not easily cause trauma to tissue due to inadvertent contact with tissue. Head (454) and the distal portion of shaft (452) are configured for insertion in bore (422) of anvil (400). Proximal surface (458) and latch shelves (436) have complementary positions and configurations such that latch shelves (436) engage proximal surface (458) when shank (420) of anvil (400) is fully seated on trocar (450). Anvil (400) is thus secured to trocar (450) through a snap fit due to latch members (430).

Trocar (450) includes an electrical contact surface (460) disposed about a portion of shaft (452) proximal to head (454). Contact surface (460) is in communication with a control circuit (not shown) of instrument (10) via a wire (462), the control circuit being configured to control firing of stapling head assembly (300). Contact surface (460) electrically isolated from shaft (452) of trocar (450).

Figure 9B:
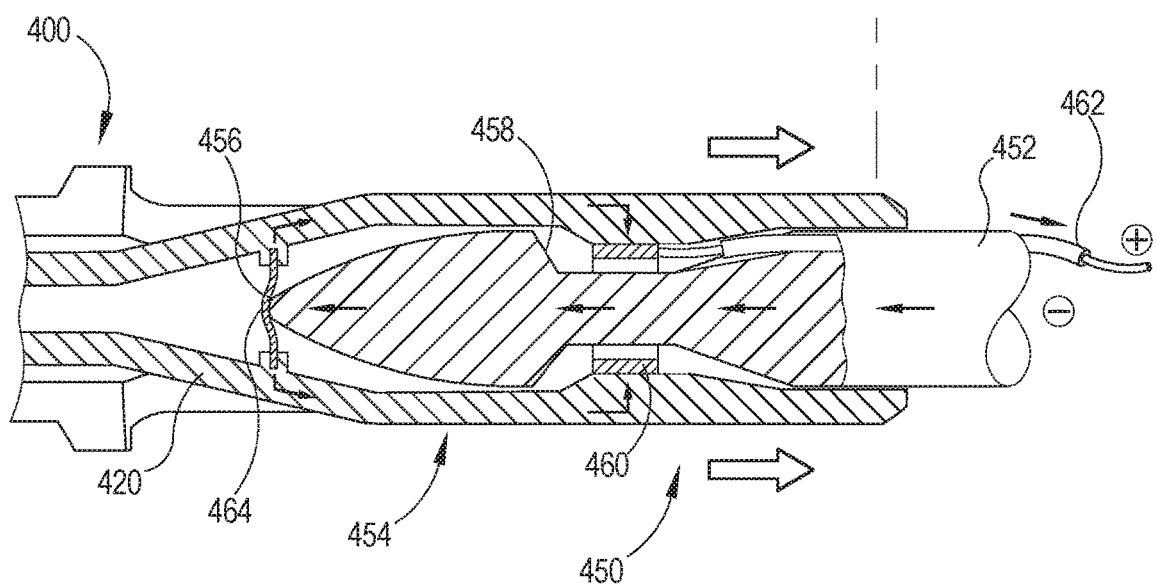
FIG. 9B depicts a cross-sectional side view of the distal end of the trocar of FIG. 8, with the circuit of FIG. 9A in a closed state.

Anvil (400) of the present example further includes an electrical contact surface (464) that is positioned within shank (420) of anvil (400). Contact surface (464) is in electrical communication with shank (420) of anvil (400). Contact surfaces (460, 464), shaft (452), shank (420), and wire (462) are configured to form part of an electrical circuit that selectively enables firing of stapling head assembly (300). In the absence of anvil (400) or with anvil (400) not properly attached to trocar (450), the electrical circuit is in an open state as shown in FIG. 9A because tip (456) of trocar (450) is not in contact with contact surface (464) of anvil (400). With anvil (400) properly attached to trocar (450) as shown in FIG. 9B, tip (456) of trocar (450) contacts contact surface (464) of anvil (400), thus providing a path for electrical continuity between shaft (452) of trocar (450) and contact surface (464) of anvil (400). In addition, shank (420) contacts contact surface (460) of trocar (450), thereby providing a path for electrical continuity between shank (420) and contact surface (460). Since shank (420) is also in electrical continuity with contact surface (464), and since contact surface (460) is in electrical continuity with wire (462), it should be understood that the above described contacts provide electrical continuity between shaft (452) of trocar (450) and wire (462) at the stage shown in FIG. 9B. This closes the circuit that enables stapling head assembly (300) to be fired. Until this circuit is closed, stapling head assembly (300) may not be fired. In other words, as in other examples herein, stapling head assembly (300) may not be fired until anvil (400) is fully seated on trocar (450).

G. Exemplary User Interface Feature of Handle Assembly

Figure 10:
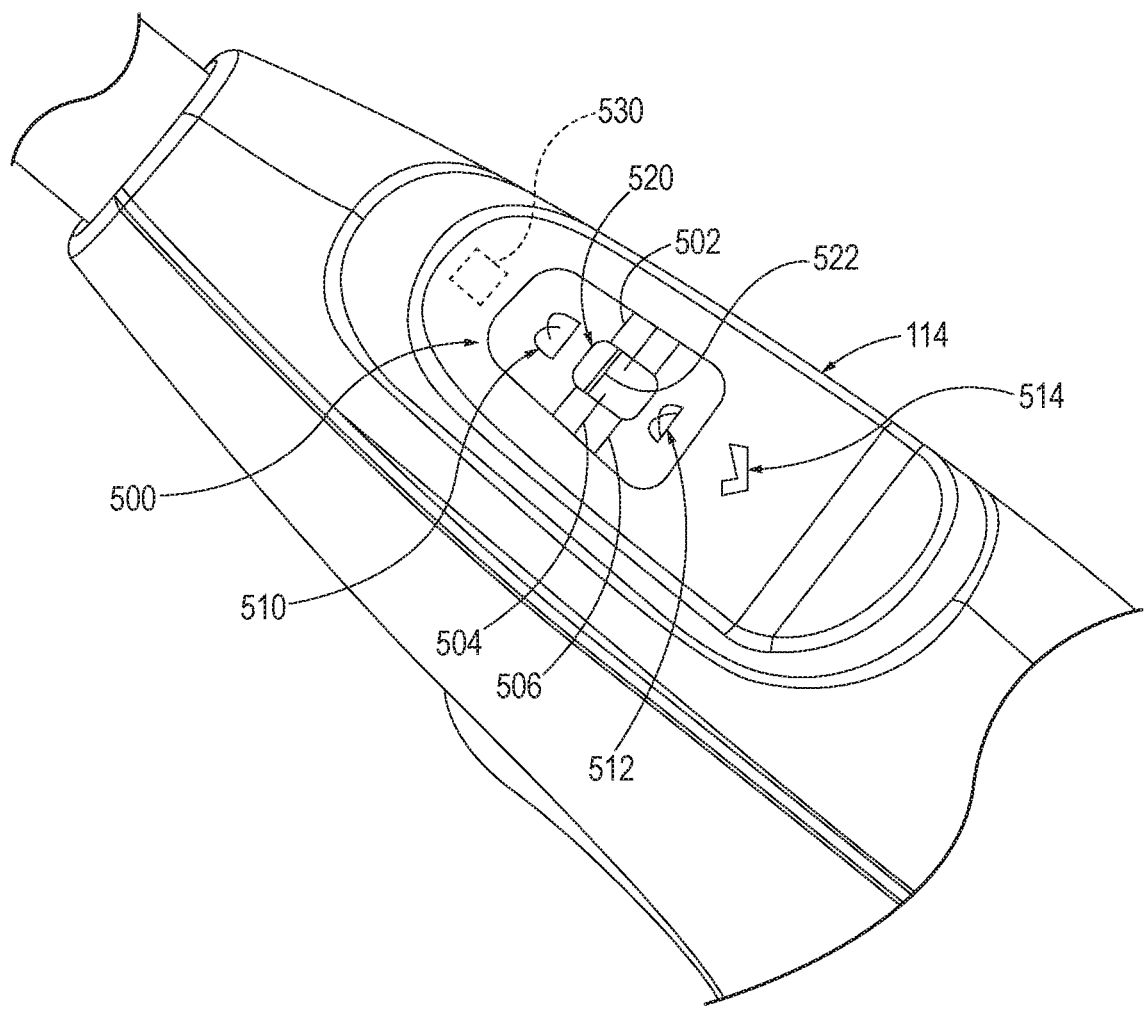
FIG. 10 depicts a perspective view of a user interface feature of the handle assembly of the circular stapler of FIG. 1.

As shown best in FIG. 10, handle assembly (100) of surgical stapling instrument (10) further includes a user interface feature (114) configured to provide the operator with visual feedback indicating the positioning of anvil (400) in relation to stapling head assembly (300) during a surgical procedure. The operator may thus observe user interface feature (114) while rotating knob (130) to confirm whether a suitable gap distance (d) between anvil (400) and stapling assembly (300) has been achieved.

User interface feature (114) of the present example includes a graphical indicator (500), which includes fixed linear indicia (502, 504, 506), graphical representations (510, 512) of staples, and a checkmark graphic (514). User interface feature (114) further defines a window (520) through which an indicator needle (522) may be viewed. In some variations, user interface feature (114) further includes a field (530) that may indicate a diameter associated with the size of stapling head assembly (300), the size of staples in stapling head assembly (300), the size of the gap defined between anvil (400) and stapling head assembly (300), and/or other information. By way of example only, field (530) may indicate a stapling head assembly (300) size of 23 mm, 25 mm, 29 mm, or 31 mm.

As the operator rotates knob (130) to adjust the longitudinal position of anvil (400) relative to stapling head assembly (300), the operator may observe the position of indicator needle (522) through window (520). Initially, indicator needle (522) may be positioned at or near the distal end of window (520). As anvil (400) continues to move proximally, indicator needle (522) will eventually move proximally relative to window (520). The operator may view the position of indicator needle (522) in relation to fixed linear indicia (502, 504, 506). The distal-most and proximal-most indicia (502, 506) may represent the boundaries of a "green zone," which is the acceptable range of distance between anvil (400) and stapling head assembly (300) for successful actuation of stapling head assembly (300). Thus, if indicator needle (522) is distal to distal-most indicia (502), the distance between anvil (400) and stapling head assembly (300) is too large; and if indicator needle (522) is proximal to proximal-most indicia (506), the distance between anvil (400) and stapling head assembly (300) is too small. Indicia (504) is longitudinally positioned between indicia (502, 506). Graphical representation (510) represents a relatively tall formed staple (e.g., suitable for use in relatively thick tissue); while graphical representation (512) represents a relatively short formed staple (e.g., suitable for use in relatively thin tissue). Graphical representations (510, 512) may thus facilitate the operator's decision, based on tissue observations or otherwise, on whether and how to achieve a desired formed staple height by selecting an appropriate corresponding spatial relationship between indicator needle (522) and indicia (502, 504, 506).

In the present example, window (520) is illuminated via a light emitting diode (LED) (not shown), further facilitating viewing of indicator needle (522) in window (520). In addition, checkmark graphic (514) is illuminated via another LED (not shown) when stapling head assembly (300) completes a stapling and cutting cycle. Thus, the operator may further rely on illumination of checkmark graphic (514) to confirm that the stapling and cutting cycle is complete, to thereby verify that it is safe to advance anvil (400) distally away from the anastomosis (70) to release the tissue and thereafter remove instrument (10) from the patient.

Circular surgical stapling instrument (10) may be further configured and operable in accordance with at least some of the teachings of U.S. Pub. No. 2017/0258471, issued as U.S. Pat. No. 10,709,452 on Jul. 14, 2020, incorporated by reference above.

II. Exemplary Circular Surgical Stapling Instrument Having Independently Controlled Closure, Stapling, and Cutting In some instances, it may be desirable to provide a version of circular surgical stapling instrument (10) that exhibits powered actuation of anvil (400) in addition to powered actuation of internal firing components of stapling head assembly (300). Furthermore, it may be desirable to provide such a version of instrument (10) with a plurality of actuators that enable independent, powered actuation of anvil (400), staple driver member (350), and knife member (340), such that the resulting closure, stapling, and cutting strokes performed by such an instrument may be controlled independently from one another in response to user input.

While the teachings below are disclosed in the context of circular surgical staplers, it will be appreciated that such teachings may be applied to other types of surgical staplers as well. By way of example only, such other staplers may include right-angle surgical staplers of the type disclosed in U.S. Pat. No. 10,045,780, entitled "Method of Applying Staples in Lower Anterior Bowel Resection," issued Aug. 14, 2018, the disclosure of which is incorporated by reference herein.

A. Overview of Circular Surgical Stapling Instrument Having Independently Controlled Actuators FIG. 11 shows an exemplary circular surgical stapling instrument (600) that exhibits a configuration and functionality of the kind described above. It will be understood that instrument (600) is similar to instrument (10) described above except as otherwise described below. Similar to instrument (10), instrument (600) generally includes a body assembly (in the form of a handle assembly (610)), a shaft assembly (630) extending distally from handle assembly (610), a stapling head assembly (640) disposed at a distal end of shaft assembly (630), and an anvil (650) configured to releasably couple with an actuatable closure member in the form of a trocar (642) of stapling head assembly (640). Anvil (650) is selectively retractable and extendable by trocar (642) relative to stapling head assembly (640) for clamping tissue against a distally facing deck surface (644) thereof. Stapling head assembly (640) is selectively operable to eject staples distally into the clamped tissue and against anvil (650), and to cut the clamped tissue with a cylindraceous knife member (not shown) similar to knife member (340) described above. Accordingly, stapling head assembly (640) and anvil (650) cooperate to define an end effector stapling assembly operable to clamp, staple, and cut tissue in response to user inputs.

Handle assembly (610) includes a casing (612) defining a pistol grip (614), a user interface (616) disposed on an upper side of casing (612) adjacent to a distal end of casing (612), and a knob (618) rotatably disposed at a proximal end of casing (612). User interface (616) and knob (618) are similar to user interface (114) and knob (130) described above except as otherwise described below. Casing (612) of the present example includes an open-ended proximal cavity (not shown) configured to releasably receive and retain a battery pack (620) similar to battery pack (120) and operable to power a motor unit (660) (see FIG. 12) housed within casing (612).

Handle assembly (610) of the present example further includes a safety member (622), a closure trigger (624), and a firing trigger (626) each movable independently relative to pistol grip (614). Actuation of closure trigger (624) is configured to activate motor unit (660) to initiate actuation of a trocar actuator (662) (see FIG. 12) and thereby effect closure of anvil (650) relative to stapling head assembly (640) to clamp tissue therebetween. Actuation of firing trigger (626) is configured to activate motor unit (660) to initiate actuation of a staple actuator (664) and a knife actuator (666) (see FIG. 12) to thereby staple and cut the clamped tissue. As described in greater detail below in connection with FIG. 13, instrument (600) is configured to control actuation of staple actuator (664) and knife actuator (666) independently in response to a single actuation of firing trigger (626). In this manner, a precise timing of the cutting stroke initiation relative to the stapling stroke initiation may be achieved.

Safety member (622) of the present example is in the form of a projection, such as a pivotable trigger similar to safety trigger (140), and is configured to directly or indirectly engage closure trigger (624) and/or firing trigger (626) to selectively block actuation thereof. For instance, safety member (622) may be configured to block actuation of closure trigger (624) until instrument (600) detects that anvil (650) has been fully attached to trocar (642). Additionally, or in the alternative, safety member (622) may be configured to block actuation of firing trigger (626) until anvil (650) has assumed a predetermined longitudinal position relative to stapling head assembly (640) that defines a particular gap distance (d) therebetween (see FIG. 7C).

Figure 12:
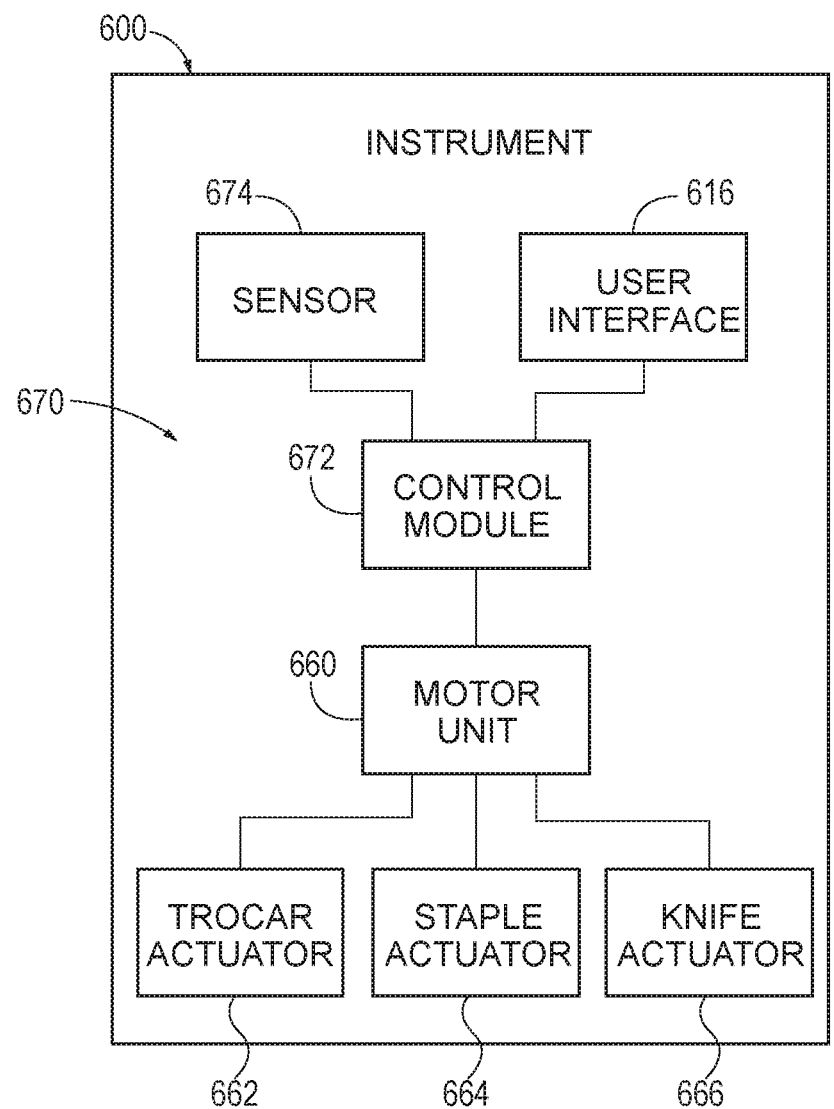
FIG. 12 depicts a schematic view of the circular stapler of FIG. 11, including a control system of the circular surgical stapler.

Actuators (662, 664, 666) of instrument (600), shown schematically in FIG. 12, are configured to operatively couple corresponding actuatable components of instrument (600) with motor unit (660). In particular, trocar actuator (662) operatively couples trocar (642) of stapling head assembly (640) with motor unit (660). Accordingly, trocar actuator (662) is configured to actuate trocar (642) and thus anvil (650) proximally and distally in response to activation of motor unit (660) when motor unit (660) is operatively engaged with trocar actuator (662). Trocar actuator (662) may include an elongate member similar to trocar actuation rod (220) combined with trocar actuation band assembly (230) of instrument (10), which is translatably disposed within shaft assembly (630).

Staple actuator (664) operatively couples a staple driver member (not shown) of stapling head assembly (640) with motor unit (660) independently of trocar actuator (662). Accordingly, staple actuator (664) is configured to actuate the staple driver member, and thus staples (not shown) housed within stapling head assembly (640), distally in response to activation of motor unit (660) when motor unit (660) is operatively engaged with staple actuator (664). Staple actuator (664) may include an elongate member similar to stapling head assembly driver (240) of instrument (10), which is translatably disposed within shaft assembly (630) independently of trocar actuator (662).

Knife actuator (666) operatively couples a cylindraceous knife member (not shown) of stapling head assembly (640) with motor unit (660) independently of trocar actuator (662) and staple actuator (664). Accordingly, knife actuator (666) is configured to actuate the knife member longitudinally in response to activation of motor unit (660) when motor unit (660) is operatively engaged with knife actuator (666). Knife actuator (666) may include an elongate member similar to stapling head assembly driver (240) of instrument (10), which is translatably disposed within shaft assembly (630) independently of trocar actuator (662) and staple actuator (664). In this manner, actuators (662, 664, 666) are configured to cooperate with motor unit (660) to provide independently actuated clamping of tissue, stapling of the tissue, and cutting of the tissue.

Knob (618) of handle assembly (610) of the present example is operatively coupled with trocar actuator (662) such that knob (618) is operable as an anvil closure bailout feature. In that regard, trocar actuator (662) is driven primarily by motor unit (660) but is also translatable longitudinally in response to rotation of knob (618), for example when motor unit (660) is deactivated or otherwise disengaged from trocar actuator (662). Accordingly, knob (618) may be rotated following partial or full proximal retraction of anvil (650) toward stapling head assembly (640) to thereby extend anvil (650) distally away from stapling head assembly (640), for example to release tissue captured therebetween. In such versions, knob (618) may be coupled with trocar actuator (662) via features similar to those described above in connection with knob (130) of instrument (10), including threaded portions (224, 226) of trocar actuation rod (220), for example. It will be understood, however, that knob (618) may be omitted from instrument (600) in some versions such that trocar actuator (662) is driven solely by motor unit (660).

Instrument (600) may be further configured and operable in accordance with at least some of the teachings of U.S. Pat. No. 9,445,816, entitled "Circular Stapler with Selectable Motorized and Manual Control," issued Sep. 20, 2016; U.S. Pat. No. 9,532,783, entitled "Circular Stapler with Select Motorized and Manual Control, Including a Control Ring," issued Jan. 3, 2017; U.S. Pat. No. 9,597,081, entitled "Motor Driven Rotary Input Circular Stapler with Modular End Effector," issued Mar. 21, 2017; U.S. Pat. No. 9,463,022, entitled "Motor Driven Rotary Input Circular Stapler with Lockable Flexible Shaft," issued Oct. 11, 2016; U.S. Pub. No. 2018/0368836, entitled "Surgical Stapler with Independently Actuated Drivers to Provide Varying Staple Heights," published Dec. 27, 2018, issued as U.S. Pat. No. 10,828,029 on Nov. 10, 2020; and/or any of the other patent references identified herein, the disclosures of which are incorporated by reference herein.

B. Exemplary Control System of Circular Surgical Stapling Instrument

As shown schematically in FIG. 12, instrument (600) further includes a control system (670) operable to control actuation of trocar actuator (662), staple actuator (664), and knife actuator (666) of instrument (600). Control system (670) includes a control module (672), motor unit (660), user interface (616), and a sensor (674) suitably arranged such that control module (672) communicates with each of motor unit (660), user interface (616), and sensor (674). Control module (672) includes a processor and is operable to store pre-programmed instrument control algorithms and receive input from user interface (616) and sensor (674). Based on these stored control algorithms and received input, control module (672) is configured to control motor unit (660) with pulse-width modulation (PWM) to drive actuation of trocar actuator (662), staple actuator (664), and knife actuator (666) independently from one another for clamping, stapling, and cutting tissue.

Motor unit (660) includes one or more motors and is operatively coupled with trocar actuator (662), staple actuator (664), and knife actuator (666). In some versions, motor unit (660) may comprise a single motor operatively coupled with and configured to drive all three actuators (662, 664, 666). In such versions, motor unit (660) may be coupled with actuators (662, 664, 666) via one or more power transmission assemblies (not shown), such as a gear assembly, various suitable types of which will be apparent to those of ordinary skill in the art in view of the teachings herein and in the incorporated references. In other versions, motor unit (660) may comprise three motors, each being dedicated to drive a respective one of actuators (662, 664, 666). In further versions, motor unit (660) may comprise two motors, a first motor of which is configured to drive trocar actuator (662) and a second motor of which is configured to drive staple actuator (664) and knife actuator (666) with assistance of a power transmission assembly. It will be understood that motor unit (660) may comprise various other quantities and arrangements of motors in other versions.

Sensor (674) is arranged within or otherwise coupled to stapling head assembly (640), shaft assembly (630), or handle assembly (610), and is operable to monitor one or more conditions of instrument (600) during use. For instance, sensor (674) may be configured to monitor translation of any one or more of actuators (662, 664, 666) and/or their adjoining components, such as trocar (642). In some such versions, sensor (674) may be mounted directly to any one of actuators (662, 664, 666) or an adjoining component thereof. In other such versions, sensor (674) may be fixedly mounted within stapling head assembly (640), shaft assembly (630), or handle assembly (610), such that actuators (662, 664, 666) and their adjoining components move relative to sensor (674).

In some versions, sensor (674) may be configured to detect secure attachment of anvil (650) to trocar (642), for example as disclosed in U.S. Pat. No. 10,307,157, incorporated by reference above. In other versions, sensor (674) may be configured to detect certain characteristics of the particular stapling head assembly (640) coupled with shaft assembly (630), such as a diameter of stapling head assembly (640) or a size of the staples (not shown) housed therein. In some such versions, sensor (674) may be configured to detect such characteristics of stapling head assembly (640) via radio-frequency identification (RFID) of electronic information stored within a tag element disposed on or within stapling head assembly (640), for example as disclosed in U.S. Prov. Pat. App. No. 62/868,457, entitled "Surgical Systems with Multiple RFID Tags," filed Jun. 28, 2019, the disclosure of which is incorporated by reference herein.

Still in other versions, sensor (674) may be in direct communication with motor unit (660). For instance, sensor (674) may be in the form of a sensor assembly that includes a current sensor operable to monitor an electrical current drawn by motor unit (660), or an encoder operable to monitor a rotational output of motor unit (660). Moreover, while only one sensor (674) is illustrated in the diagram of FIG. 12, it will be understood that sensor (674) may comprise a plurality of sensors, where each individual sensor (674) is configured to monitor and communicate with control module (672) regarding a respective one or more conditions of instrument (600). Furthermore, it will be understood that sensor (674) may comprise various suitable types of sensors readily apparent to those of ordinary skill in the art in view of the teachings herein and not otherwise described herein.

User interface (616) is similar to user interface (114) described above, except that user interface (616) is further configured to receive and communicate user input to control module (672). In that regard, user interface (616) may include one or more buttons, dials, other actuatable elements, or displayed graphics that are selectable by a user to indicate certain information pertaining to a surgical procedure to be performed or to stapling head assembly (640). By way of example only, such information may include any of the following: a desired staple formation height; a corresponding gap between anvil (650) and stapling head assembly (640) to which anvil (650) should be actuated during closure; a type or nominal thickness of tissue being fired upon with instrument (600); and/or a diameter of stapling head assembly (640). Such information, in combination with information provided by sensor (674), may be used by control module (672) to adjust strokes and/or rates of actuation of actuators (662, 664, 666), and/or to adjust timing pauses between the powered actuations of actuators (662, 664, 666) to ensure optimal clamping, stapling, and cutting of tissue during a procedure, for example as described in greater detail below.

C. Exemplary Method for Controlling Circular Surgical Stapler

Figure 13:
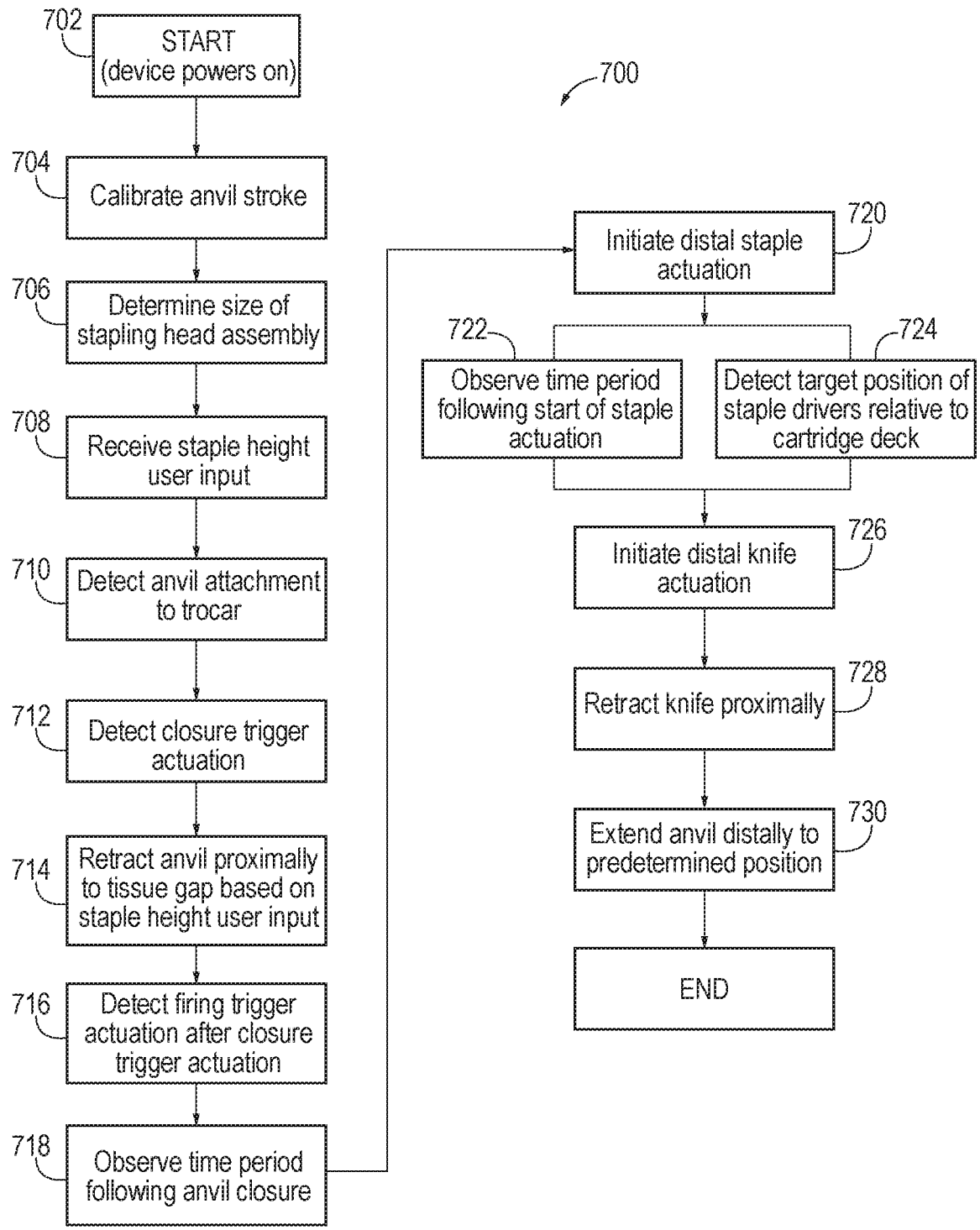
FIG. 13 depicts a diagrammatic view of an exemplary method for controlling the circular stapler of FIG. 11 via the control system of FIG. 12.

FIG. 13 shows an exemplary method (700) for controlling circular surgical stapling instrument (600) via control system (670) shown in FIG. 12. At step (702), instrument (600) powers on in response to being energized by battery pack (620), for example when battery pack (620) is fully inserted into the proximal end of handle assembly (610) after instrument (600) is removed from product packaging. Upon removal from the packaging, anvil (650) is already secured to trocar (642) and is in a fully open state, and a staple retainer (not shown) is secured to deck surface (644).

After instrument (600) powers on in the present example, control module (672) enters an anvil stroke calibration mode at step (704), which may occur automatically or in response to a user input, for example provided via user interface (616). In this calibration mode, control module (672) activates motor unit (660) to drive trocar actuator (662) to retract trocar (642) proximally and thereby close anvil (650) against the staple retainer, or alternatively against deck surface (644) in the event that the staple retainer has been removed. Control module (672) may detect that anvil (650) has reached a closed position by detecting via sensor (674) an increase in the electrical current load of motor unit (660) upon contact of anvil (650) with the staple retainer or deck surface (644). Control module (672) observes the stroke (i.e., longitudinal displacement) of anvil (650) during this retraction process and compares it to an expected stroke of anvil (650). Based on this comparison and any differences observed between the two stroke values, control module (672) then calibrates an actuation algorithm that is executed to activate motor unit (660) to trocar actuator (662), and thereby ensure precise actuations of anvil (650) thereafter during a surgical procedure. In addition, or in the alternative, calibration of the anvil stroke may be performed by control module (672) in real time during a surgical procedure when anvil (650) is being retracted to clamp tissue. Such calibration of the anvil stroke is described in further detail in U.S. patent application Ser. No. 16/574,773, entitled "Method for Calibrating Movements of Actuated Members of Powered Surgical Stapler," filed on Sep. 18, 2019, published as U.S. Pub. No. 2021/0077111 on Mar. 18, 2021, the disclosure of which is incorporated by reference herein. It will be understood that the strokes of one or more other actuatable members of instrument (600) may be calibrated in a similar manner before or during a surgical procedure, and also that the calibration of the anvil closure stroke may be applied by control module (672) to also calibrate the stapling stroke and/or the cutting stroke of instrument (600).

At step (706), control module (672) determines a diameter of stapling head assembly (640). As described above, stapling head assembly (640) may be releasably attached to shaft assembly (630) such that stapling head assemblies (640) of various diameters may be interchangeably coupled with the distal end of shaft assembly (630) depending on a lumen size of the tissue structure being operated on with instrument (600). Control module (672) is configured to make this size determination based on user input provided via user interface (616) and/or information provided by sensor (674), for instance when sensor (674) is configured to detect the size of stapling head assembly (640) in the manner described above.

At step (708), control module (672) receives from user interface (616) input that indicates a desired height of staples to be formed in tissue, as selected by the operator via user interface (616). Control module (672) equates this staple height to a corresponding gap distance (d) (see FIG. 7C) to be established between anvil (650) and deck surface (644) of stapling head assembly (640) at a closed position of anvil (650), in order to achieve the selected staple height.

While steps (704, 706, 708) are shown in FIG. 13 as being performed in a particular order, it will be appreciated that these steps (704, 706, 708) may be performed in a variety of orders relative to one another following the powering on of instrument (600) in step (702) and before the actuation of staple actuator (664) described below.

Following completion of steps (704, 706, 708), the operator detaches anvil (650) from trocar (642) and proceeds to position anvil (650) within a first tubular tissue structure of a patient and separately position stapling head assembly (640) within a second tubular tissue structure of the patient. The operator then attaches anvil (650) to trocar (642) within the patient, for example as shown in FIGS. 7A-7B described above, at which point control module (672) detects at step (710) that the attachment has been made. Such detection may be made by sensor (674), which communicates a corresponding signal to control module (672).

At step (712), control module (672) detects that closure trigger (624) has been actuated by the operator. Control module (672) then proceeds to step (714) and directs motor unit (660) to drive trocar actuator (662) to actuate trocar (642) proximally and thereby retract anvil (650) to a closed position at which the selected staple height and corresponding gap distance (d) are achieved. In some versions, control module (672) may be configured to initiate retraction of trocar (642) and anvil (650) only in response to an actuation of closure trigger (624) that occurs after attachment of anvil (650) to trocar (642) has been detected at step (710). The operator may monitor the retraction of anvil (650) toward its closed position via visual indicia and/or displayed graphics of user interface (616).

Additionally, in some versions, control module (672) may control motor unit (660) to retract anvil (650) proximally through the anvil closure stroke in two sequential stages. For instance, control module (672) may direct motor unit (660) to retract anvil (650) through a first portion of the anvil closure stroke, at which point control module (672) pauses activation of motor unit (660) for a predetermined period of time (e.g., several seconds). At the end of this wait period, control module (672) reactivates motor unit (660) to continue retracting anvil (650) through the remaining portion of the anvil closure stroke to its closed position. Inclusion of such a pause in the retraction of anvil (650) may enable the tissue being compressed between anvil (650) and deck surface (644) to at least partially settle (or "creep"). Advantageously, this settling of tissue yields a reduction of the axial extension load on trocar (642) and the resulting electrical current load of motor unit (660) as anvil (650) advances proximally to its fully closed position defined by the target staple height input provided by the user in step (708).

At step (716), control module (672) detects that firing trigger (626) has been actuated by the operator following completion of the anvil closure stroke. In the present example, in response to detecting this actuation, control module (672) observes completion of a predetermined period of time measured from completion of the anvil closure stroke, during which staple actuator (664) and knife actuator (666) remain stationary. This wait period after anvil closure enables the clamped tissue to settle (or "creep") into its fully compressed state before stapling head assembly (640) is fired, thus reducing the axial loads on staple actuator (664) and knife actuator (666), and the resulting current loads of motor unit (660), during the respective stapling and cutting sequences. It will be understood that this wait period may be omitted in some versions.

Upon completion of the wait period denoted in step (718), control module (672) initiates distal actuation of the staple driver member (not shown) at step (720) to begin stapling the clamped tissue. In particular, control module (672) activates motor unit (660) to engage and drive staple actuator (664) to actuate the staple driver member distally through stapling head assembly (640) and thereby drive staples into tissue and against anvil (650), for example similar to the manner shown in FIG. 7D. Upon initiating actuation of staple actuator (664), control module (672) at step (722) observes another predetermined period of time during which motor unit (660) continues to drive staple actuator (664) through the stapling stroke. Simultaneously, at step (724) control module (672) communicates with sensor (674) to detect when the staple driver member reaches a predetermined longitudinal position within stapling head assembly (640). Such a position may correspond to the point at which individual staple drivers (not shown), similar to staple drivers (352) described above, reach deck surface (644) such that the staples are at least partially formed within the clamped tissue. This process is described in further detail in U.S. patent application Ser. No. 16/574,797, entitled "Method for Controlling Cutting Member Actuation for Powered Surgical Stapler," filed on Sep. 18, 2019, published as U.S. Pub. No. 2021/0077112 on Mar. 18, 2021, the disclosure of which is incorporated by reference herein.

In response to detecting completion of the predetermined time period of step (722) and/or detecting at step (724) that the staple driver member has reached the predetermined longitudinal position, control module (672) then initiates distal actuation of the knife member (not shown) at step (726) to begin cutting the tissue. In particular, control module (672) activates motor unit (660) to engage and drive knife actuator (666) to actuate the knife member distally through stapling head assembly (640) and thereby cut the tissue, for example similar to the manner shown in FIG. 7D.

As noted above, delaying initiation of the cutting stroke relative to initiation of the stapling stroke, as enabled by independent actuation of staple and knife actuators (662, 664, 666), ensures at least partial formation of staples within the tissue before tissue cutting commences. Advantageously, this approach enables the staples to anchor within the clamped tissue before cutting and thereby prevent lateral shifting of the tissue and resulting malformation of the staples when the knife member is driven distally.

The end of the distal cutting stroke of the knife member may correspond to a point at which the knife member breaks a washer (not shown) within anvil (650) similar to washer (417) described above. Upon completion of the distal cutting stroke, control module (672) at step (728) directs motor unit (660) to retract the knife member proximally back into stapling head assembly (640). In some versions, knife member distal extension and subsequent proximal retraction may be achieved by powering motor unit (660) through a continuous, uniform range of motion, for example as disclosed in U.S. Pub. No. 2017/0258471, issued as U.S. Pat. No. 10,709,452 on Jul. 14, 2020, incorporated by reference above. In other versions, control module (672) may be programmed to communicate with sensor (674) to detect completion of the distal cutting stroke, and thereafter specifically direct motor unit (660) to drive knife actuator (666) in an alternative manner to retract the knife member proximally. In any of such versions, sensor (674) may comprise an encoder configured to monitor a rotational output of motor unit (660).

Simultaneously with or subsequently to knife retraction step (728), control module (672) at step (730) directs motor unit (660) to drive trocar actuator (662) distally to thereby extend anvil (650) distally to a predetermined position relative to deck surface (644) of stapling head assembly (640). This distal extension enables the stapled tissue to be released from between anvil (650) and stapling head assembly (640) so that instrument (600) may be withdrawn from the patient while anvil (650) remains attached to trocar (642).

III. Anvil Sensing and Retention

There are several tasks that the user may accomplish without visualization while using instrument (10, 600). For example, one such task may include ensuring a sufficient connection between anvil (400, 650) with trocar (330, 450, 642), such that anvil (400, 650) is sufficiently held during movement of the trocar (330, 450, 642). Another task may include opening the instrument (10) after firing of instrument (10) without losing track of anvil (400, 650). Yet another task may include emergency release of anvil (400, 650) from trocar (330, 450, 642) in the unlikely event of an issue arising during use.

In some instances, it may be beneficial to continuously know the position of anvil (400, 650), while anvil (400, 650) is disposed within the patient. As such, it may be undesirable to completely release anvil (400, 650) from trocar (330, 450, 642) during, or even after, a particular surgical procedure. For example, completely releasing anvil (400, 650) from trocar (330, 450, 642) may require the user to locate and subsequently "fish out" anvil (400, 650) from the patient. Fishing out anvil (400, 650) from the patient may increase the duration of the procedure. Additionally, if anvil (400, 650) inadvertently decouples from trocar (330, 450, 642), this may render erroneous all data acquired by the processor during closure (e.g., for stroke/rate calibration purposes). With particular reference to instrument (10), it is undesirable for latch shelves (436) of anvil (400) to become decoupled from proximal surface (338) of trocar (330) during closing and/or firing.

As such, after firing is completed, it is desirable to space anvil (400, 650) apart from deck surface (322, 644) to release tissue from anvil (400, 650) and enable withdrawal of instrument (10, 600) from the patient. In some instances, this may be performed by extending trocar (330, 450, 642) by an arbitrary distance by blindly spacing anvil (400, 650) apart from deck surface (322, 644). For example, this may be performed by the user manually actuating knob (130), which is disposed at a proximal end of handle assembly (100). It would be desirable that upon completion of firing, anvil (400, 650) be extended to a pre-determined distance away from deck surface (322, 644), with a subsequent indication provided to the user that instrument (600) is ready to be withdrawn from the patient.

A. Exemplary Stapling Head Assembly and Anvil

As previously described above with reference to FIGS. 11-12, instrument (600) includes a body assembly (e.g. handle assembly (610)), shaft assembly (630), stapling head assembly (640), and anvil (650). Handle assembly (610) includes motor unit (660) to power instrument (600). For example, as described above with reference to FIGS. 11-12, motor unit (660) may include one or more motors to power one or more actuators (e.g. actuators (662, 664, 666)). Shaft assembly (630) extends distally from handle assembly (610).

FIGS. 14-17H show an exemplary alternative stapling head assembly (800) and an exemplary alternative anvil (802) configured for use with instrument (600). For example, stapling head assembly (800) may be used in place of stapling head assembly (640) and anvil (802) may be used in place of anvil (650). Stapling head assembly (800) may be similar to stapling head assembly (300, 640), except as where otherwise described below. Similarly, anvil (802) may be similar to anvil (400, 650), except as where otherwise described below. Stapling head assembly (800) is positioned at a distal end of shaft assembly (630) similar to stapling head assembly (640). Stapling head assembly (800) includes at least one annular array of staples (not shown), but which may be similar to staples (90) that are formed into an annular array. Stapling head assembly (800) also includes a staple driver (not shown), but which may be similar to staple driver (352). Staple driver (352) is configured to drive at least one annular array of staples (90) against anvil (802) to deform staples (90).

As shown in FIGS. 14-15, stapling head assembly (800) includes a trocar (804) and a lockout assembly (806). Trocar (804) includes a shaft (808), an actuating feature (810), and at least one retention feature (shown as first and second retention features (812, 814)). Shaft (808) defines a longitudinal axis (LA) of trocar (804). Shaft (808) of trocar (804) includes a wall (816) having inner and outer surfaces (818, 820). Inner surface (818) of wall (816) defines a lumen (822) of shaft (808). Shaft (808) also includes apertures (823) extending through shaft (808) that allow first and second retention features (812, 814) to extend through shaft (808) of trocar (804). Shaft (808) also includes a pointed tip (824) adjacent a distal end (826). Similar to pointed tip (336), pointed tip (824) is not sharp and is not intended to easily cause trauma to tissue due to inadvertent contact with tissue. Actuating feature (810) is configured to move along longitudinal axis (LA) within lumen (822) to move first and second retention features (812, 814) of trocar (804) between a contracted position and an expanded position as described in greater detail below with reference to FIGS. 17A-17H. As shown in FIG. 14, first and second retention features (812, 814) are spaced apart along longitudinal axis (LA) of shaft (808) of trocar (804).

As shown in FIG. 14, anvil (802) includes a shaft (828) and a head (830) (see FIGS. 16A-16I) extending distally from shaft (828). Shaft (828) includes a wall (832) having inner and outer surfaces (834, 836). Inner surface (834) of wall (832) defines a lumen (838). Inner surface (818) of wall (816) includes an outwardly tapering portion (840) adjacent a proximal end (842) of shaft (828) of anvil (802). Anvil (802) may include at least one interior recess. As shown, inner surface (834) of anvil (802) includes first and second interior recesses (844, 846) that are spaced apart from one another along longitudinal axis (LA). While first and second interior recesses (844, 846) are shown, any suitable number, shapes, and sizes of interior recesses are envisioned. For example, if first and second retention features (812, 814) include annular rings, first and second interior recesses (844, 846) may be annularly shaped to accommodate the annular rings. While not shown, first and second interior recesses (844, 846) may extend completely through wall (832). Actuating feature (810) may be an active motor driven actuator, which is activated either manually by the user or automatically when anvil (802) is fully inserted onto trocar (804) of instrument (600).

As shown in FIG. 15, motor unit (660) as instructed by control module (672) is configured to actuate actuating feature (810) to move first and second retention features (812, 814) of trocar (804) once the lockout assembly (806) is in a non-locked out configuration. Actuating feature (810) is operatively coupled with motor unit (660). First motor is configured to power trocar (804) to move actuating feature (810). Second motor is configured to drive staple actuator (664) that drives staple driver (not shown). Actuating feature (810) provides radial displacement of first and second retention features (812, 814) relative to respective first and second interior recesses (844, 846) formed in inner surface (834) of shaft (828) of anvil (802). While resiliently biased projections (848) are shown in FIG. 14, it is also envisioned that first and second retention features (812, 814) may include a variety of biasing features other than resiliently biased projections (848). For example, first and second retention features (812, 814) may include resiliently biased annular rings (e.g. first and second annular rings) among other suitable resiliently biased projections.

FIGS. 14-15 show an exemplary lockout assembly. Lockout assembly (806) determines whether anvil (802) is fully inserted into trocar (804). Particularly, lockout assembly (806) is configured to prevent activation of actuating feature (810) in response to anvil (802) not being fully coupled with trocar (804). Conversely, lockout assembly (806) is configured to permit activation of actuating feature (810) in response to coupling of anvil (802) with trocar (804) such that first and second retention features (812, 814) are permitted to move to the expanded position. FIG. 14 shows trocar (804) as including a first electrical contact (850) and anvil (802) as including a second electrical contact (852). First and second electrical contacts (850, 852) are configured to detect loading, connection, and retraction of anvil (802) relative to shaft (808) of trocar (804). As shown, first electrical contact (850) is disposed on an outer surface (820) of shaft (808) of trocar (804), and second electrical contact (852) is disposed on inner surface (834) of shaft (828) of anvil (802). As shown, first electrical contact (850) includes first and second portions (854a-b) electrically coupled to first and second wires (856a-b) respectively. It is envisioned that first electrical contact (850) may include more or fewer portions than first and second portions (854a-b). While lockout assembly (806) is shown in FIGS. 14-15 as an electrical switch, it is also envisioned that lockout assembly (806) may be implemented using a variety of different features, including one or more sensors.

FIG. 15 shows a schematic view of a portion of lockout assembly (806) of FIG. 14, showing first portion (854a) including an insulated portion (858). Insulated portion (858) may be coupled with outer surface (820) of trocar (804) using a variety of methods. As shown in FIGS. 14-15, an electrical signal (e.g. current) may be passed through first wire (856a) to first electrical contact (850), then from first electrical contact (850) to second electrical contact (852), then from second electrical contact (852) to second wire (856b), and then from second wire to control module (672). Alternatively, a single wire may be utilized as shown and described above with reference to FIGS. 9A-9B, where current may initially pass through trocar (804) and out through first wire (856a).

B. Exemplary Method

Figure 17A:
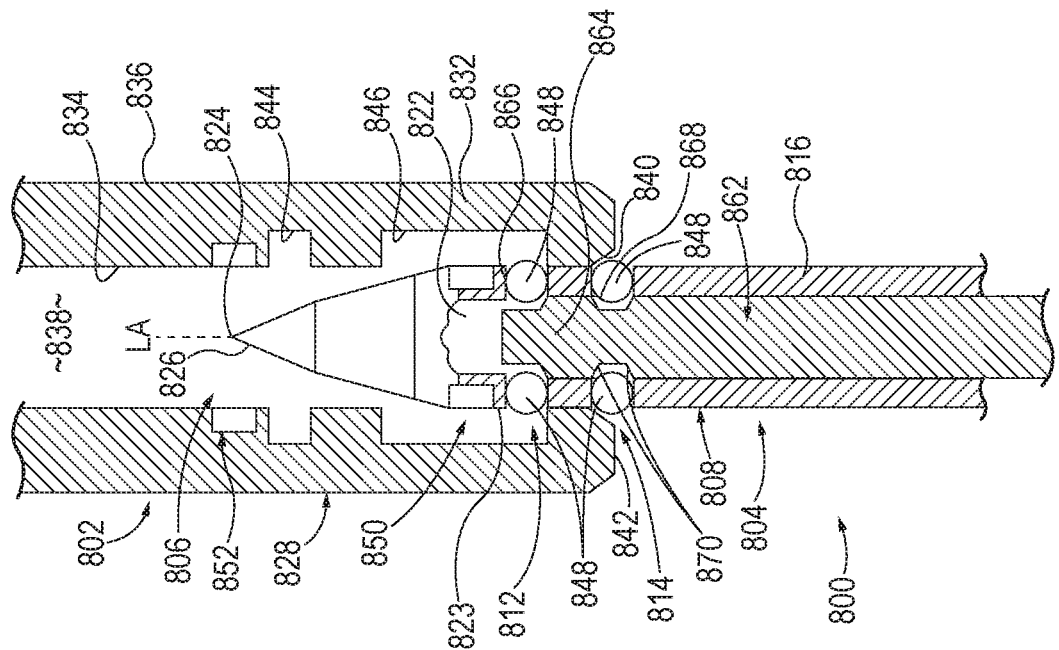
FIG. 17A depicts a detailed portion of FIG. 16A, with the anvil separated from the trocar and the lockout assembly in a locked-out configuration.
Figure 16A:
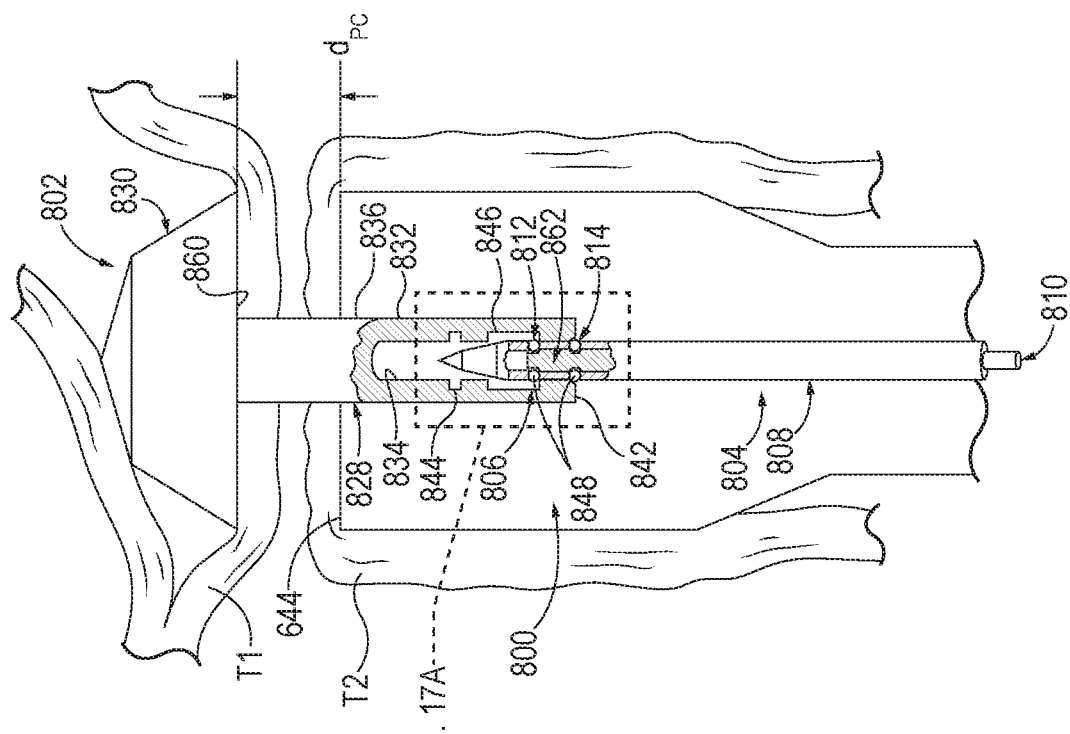
FIG. 16A depicts a cross-sectional side view of the anvil and the trocar of the stapling head assembly of FIG. 14, with the anvil positioned within a first portion of tissue and the trocar positioned in a second portion of tissue that is spaced from the first portion of tissue, such that the anvil is separated from the trocar and the lockout assembly is in a locked out configuration.

An exemplary method of coupling anvil (802) with trocar (804) of stapling head assembly (800) is now described with reference to FIGS. 16A-17H. FIG. 16A and FIG. 17A show anvil (802) separated along longitudinal axis (LA) from trocar (804) prior to coupling anvil (802) with trocar (804). FIG. 16A shows a cross-sectional side view of anvil (802) and trocar (804) of stapling head assembly (800) of FIG. 14, with anvil (802) positioned within a first portion (T1) of tissue and trocar (804) positioned in a second portion (T2) of tissue that is spaced from first portion (T1) of tissue along longitudinal axis (LA). Particularly, a proximal surface (860) of head (830) of anvil (802) is spaced at a pre-compressed distance ($d_{PC}$) from deck surface (644). In the contracted position, shaft (808) of trocar (804) is configured to move along longitudinal axis (LA) relative to anvil (802) using motor unit (660).

FIG. 17A shows a detailed portion of FIG. 16A, where lockout assembly (806) is in the locked-out configuration. Particularly, since anvil (802) is not fully coupled with trocar (804), first and second electrical contacts (850, 852) are not aligned, causing that electrical switch to be open. When the electrical switch is open, the electrical signal cannot pass from first electrical contact (850) to second electrical contact (852). As a result, first and second retention features (812, 814) of trocar (804) are prevented from engaging anvil (802). As shown and described with reference to FIGS. 17A-17H, actuating feature (810) includes an actuating rod (862). A distal portion (864) of actuating rod (862) includes first and second narrow portions (866, 868) having a reduced cross-sectional area. First and second narrow portions (866, 868) are bounded by angled surfaces (870). First and second retention features (812, 814) are shown as being at least partially disposed within respective first and second narrow portions (866, 868) in the contracted position, allowing trocar (804) to move along longitudinal axis (LA) relative to anvil (802). As a result, in the contracted position, first retention feature (812) is spaced from first interior recess (844) and second retention feature (814) is spaced from second interior recess (846).

FIG. 16B shows a cross-sectional side view of anvil (802) and trocar (804) of stapling head assembly (800) of FIG. 14, with trocar (804) fully inserted into anvil (802). For example, trocar (804) may be advanced distally using trocar actuator (662). Similar to FIG. 16A, second portion (T2) of tissue that is spaced from first portion (T1) of tissue along longitudinal axis (LA). Particularly, proximal surface (860) of head (830) of anvil (802) is spaced at a pre-compressed distance ($d_{PC}$) from deck surface (644). FIG. 17B shows a detailed portion of FIG. 16B, with trocar (804) fully inserted into anvil (802), first and second retention features (812, 814) in the contracted position. Lockout assembly (806) is in a non-locked out configuration since anvil (802) is fully coupled with trocar (804). As a result, first and second electrical contacts (850, 852) are aligned such that electrical switch is closed. When the electrical switch is closed, the electrical signal can pass from first electrical contact (850) to second electrical contact (852). In the contracted position, first and second retention features (812, 814) of trocar (804)

are spaced from first and second interior recesses (844, 846) of anvil (802). First and second retention features (812, 814) are ready to move, but not yet moved, in a transverse direction relative to longitudinal axis (LA) of shaft (808) from the contracted position to the expanded position. As shown, the transverse direction is perpendicular to longitudinal axis (LA) of shaft (808) of trocar (804). However, other transverse directions are also envisioned.

Figures 16C, 17C:
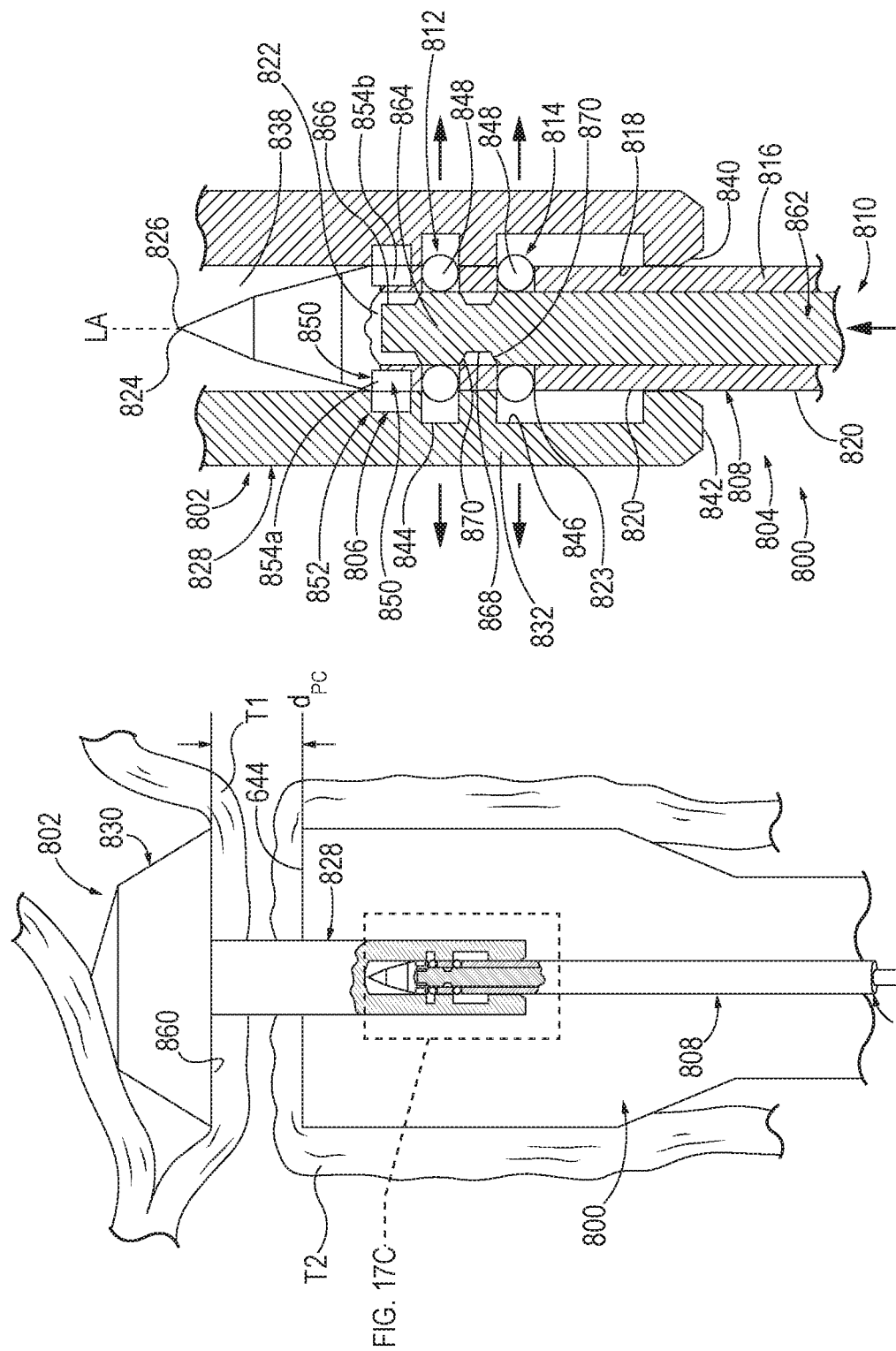
FIG. 16C depicts a cross-sectional side view of the anvil and the trocar of the stapling head assembly of FIG. 14.
FIG. 17C depicts a detailed portion of FIG. 16C, with the first and second retention features moved to an expanded position using an actuating rod.

FIG. 16C shows a cross-sectional side view of anvil (802) and trocar (804) of stapling head assembly (800) of FIG. 14. Similar to FIGS. 16A-16B, second portion (T2) of tissue is spaced from first portion (T1) of tissue along longitudinal axis (LA). Particularly, proximal surface (860) of head (830) of anvil (802) is spaced at the pre-compressed distance ($d_{PC}$) from deck surface (644). FIG. 17C shows a detailed portion of FIG. 16C, with first and second retention features (812, 814) moved to the expanded position using actuating rod (862). Actuating rod (862) is driven using motor unit (660). Motor unit (660) may be drive actuating rod (862) separately from trocar actuator (662) that translates trocar (804) using a signal from control module (672). Angled surfaces (870) of distal portion (864) of actuating rod (862) contact first and second retention features (812, 814) to outwardly push first and second retention features (812, 814) into first and second interior recesses (844, 846) of anvil (802). In the expanded position, first and second retention features (812, 814) of trocar (804) are disposed at least partially within respective first and second interior recesses (844, 846) of anvil (802). Particularly, as shown, first retention feature (812) of trocar (804) is disposed at least partially within first interior recess (844) and second retention feature (814) is disposed at least partially within second interior recess (846). In the expanded position, shaft (808) of trocar (804) is configured to move together as a unit with shaft (828) of anvil (802) along longitudinal axis (LA).

FIG. 16D shows a cross-sectional side view of anvil (802) and trocar (804) of stapling head assembly (800) of FIG. 14, with shaft (828) of anvil (802) moved proximally towards anvil (802) of stapling head assembly (800) using trocar actuator (662) to compress first and second portions (T1, T2) of tissue together to the closed position. As shown, proximal surface (860) of head (830) of anvil (802) is spaced at a compressed distance ($d_C$) away from deck surface (644), which is less than the pre-compressed distance ($d_{PC}$). FIG. 17D shows a detailed portion of FIG. 16D, with first and second retention features (812, 814) in the expanded position such that trocar (804) and anvil (802) are proximally withdrawn as a unit to the closed position.

Figures 16E, 17E:
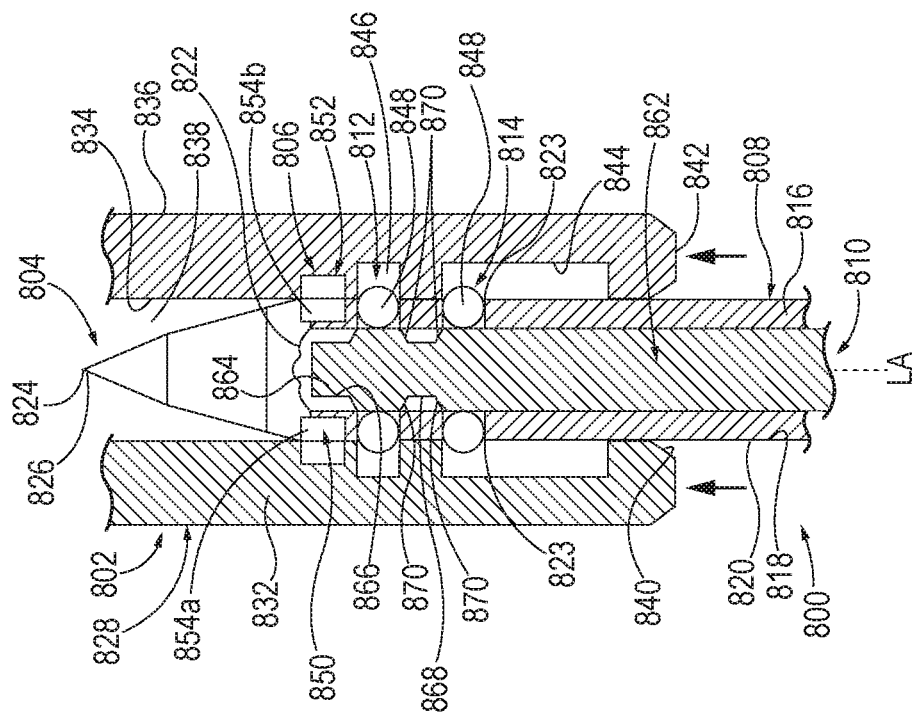
FIG. 16E depicts a cross-sectional side view of the anvil and the trocar of the stapling head assembly of FIG. 14, after the stapling head assembly is actuated to sever and staple the first and second portions of tissue.
FIG. 17E depicts a detailed portion of FIG. 16E, with the stapling head assembly actuated to sever and staple the first and second portions of tissue.

FIG. 16E shows stapling head assembly (800) actuated to sever and staple first and second portions (T1, T2) of tissue. Firing instrument (600) forces at least one annular array of staples (90) through first and second portions (T1, T2) of tissue of the patient. As previously described, actuation of firing trigger (626) is configured to activate motor unit (660) to initiate actuation of a staple actuator (664) and knife actuator (666) (see FIG. 12) to thereby staple and cut the clamped tissue. As described in greater detail below in connection with FIG. 13, instrument (600) is configured to control actuation of staple actuator (664) and knife actuator (666) independently in response to a single actuation of firing trigger (626). FIG. 16E shows a cross-sectional side view of anvil (802) and trocar (804) of stapling head assembly (800) of FIG. 14, after stapling head assembly (800) is actuated to sever and staple first and second portions (T1, T2) of tissue. FIG. 17E shows a detailed portion of FIG. 16E.

After the firing, it may be desirable to move anvil (400, 650) to a predetermined distance away from deck surface (644). For example, it may be beneficial for instrument (600) to open to a known maximum height. Additionally, it may be desirable to have active detection and sensing of anvil (400, 650) as well as a means for releasing anvil (400, 650) in cases of emergency and partially to release tissue once firing of instrument (10, 600) is complete. It may be desirable to include active electro-mechanical anvil retention and release systems, which may work together with detection and sensing of anvil (400, 650). FIGS. 16F, 16H, and 16I the method may include translating trocar (804) along longitudinal axis (LA) of trocar (804) between a closed position, a first tissue release position, and/or a second tissue release position as described below. For example, the method may include extending trocar (804) to the first tissue release position shown in FIG. 16F, or a second tissue release position shown in FIG. 16H, while trocar (804) is still coupled with anvil (802). This prevents the user from having to fish out anvil (802) as previously described. In the expanded position, trocar (804) and anvil (802) may translate together as a fixed unit along longitudinal axis (LA) between the closed position, the first tissue release position, and the second tissue release position.

FIG. 16F shows a cross-sectional side view of anvil (802) and trocar (804) of stapling head assembly (800) of FIG. 14, with trocar (804) and anvil (802) distally advanced withdrawn together as a unit to the first tissue release position after severing and stapling the tissue. First and second retention features (812, 814) are shown in the expanded position. FIG. 17F shows a detailed portion of FIG. 16F, with trocar (804) fully inserted into anvil (802), first and second retention features (812, 814) in the expanded position, and actuating rod (862) prepared to be proximally withdrawn. As shown, the closed position and the first tissue release position are separated by a first distance ($d_{TR1}$) that is greater than the clamped distance ($d_C$).

Figure 17G:
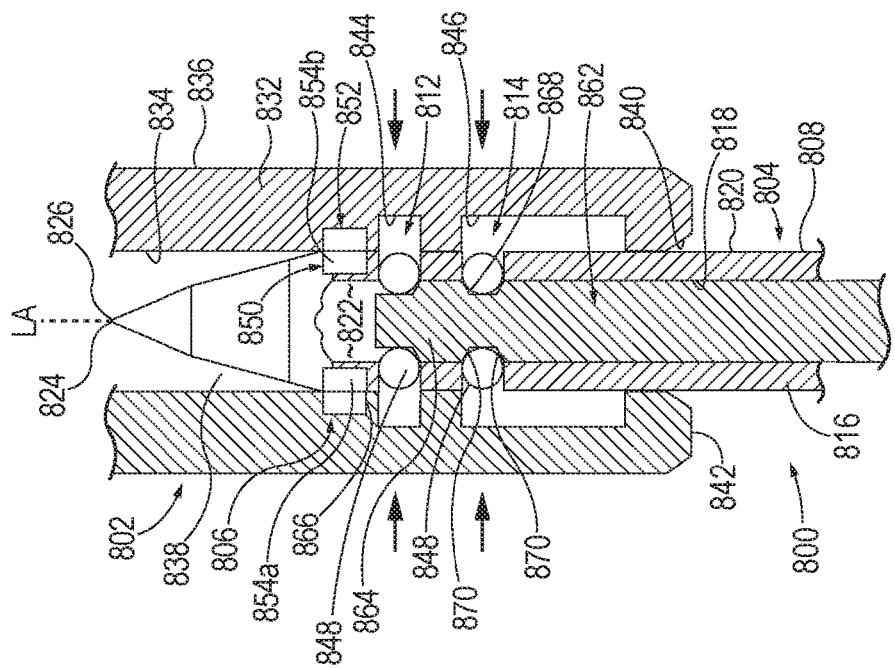
FIG. 17G depicts a detailed portion of FIG. 16G, with the trocar fully inserted into the anvil and the first and second retention features in a contracted position using the actuating rod.
Figure 16G:
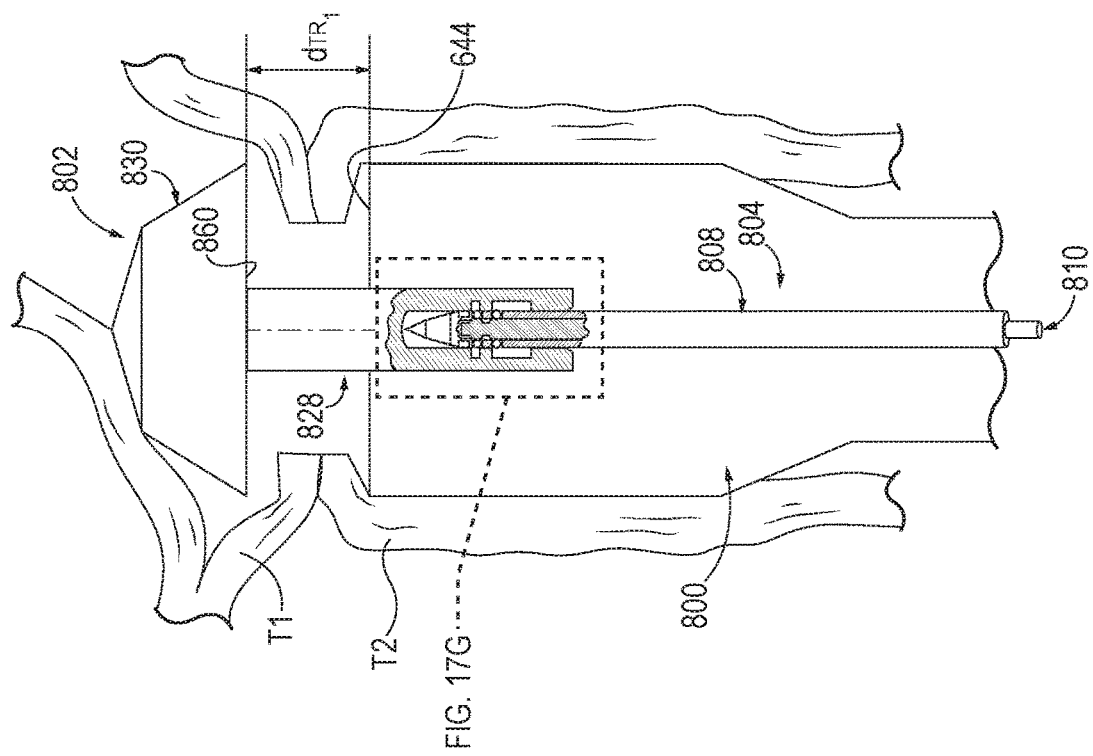
FIG. 16G depicts a cross-sectional side view of the anvil and the trocar of the stapling head assembly of FIG. 14, with the anvil separated from the deck member at the first tissue release position.

FIG. 16G shows a cross-sectional side view of anvil (802) and trocar (804) of stapling head assembly (800) of FIG. 14 in the first tissue release position after actuating rod (862) is proximally withdrawn. Motor unit (660) may be drive actuating rod (862) separately from trocar actuator (662) that translates trocar (804) using a signal from control module (672). Anvil (802) is separated from deck surface (644) at the first tissue release position and first and second retention features (812, 814) are in the contracted position. Particularly, first and second retention features (812, 814) are moved from the contracted position to the expanded position by activating actuating rod (862) after determining anvil (802) is fully inserted into trocar (804). FIG. 17G shows a detailed portion of FIG. 16G, with trocar (804) fully inserted into anvil (802) and first and second retention features (812, 814) in the contracted position using actuating rod (862). As shown in FIG. 17G, first and second retention features (812, 814) are releasable from anvil (802) enabling removal. The release of anvil (802) has a first and second amount of release. The first tissue release position may be a partial opening of anvil (8020) enabling removal of anvil (802) from tissue by the user. The second tissue release position is a full release in the event of an unexpected issue encountered by instrument (600). Partial release not fully releasing anvil (802).

FIG. 16H shows a cross-sectional side view of anvil (802) and trocar (804) of stapling head assembly (800) of FIG. 14 in the second tissue release position. Instrument (600) may move anvil (802) to the second tissue release position without first stopping at the first tissue release position shown in FIGS. 16F-16G. Actuating feature (810) may automatically actuate first and second retention features (812, 814) to move first and second retention features (812, 814) to the contracted position. At the second release position, actuating feature (810) is configured to manually or automatically actuate first and second retention features (812, 814). At the second tissue release position, first and second retention features (812, 814) may be automatically actuated using actuating feature (810), which may be motor driven, to move first and second retention features (812, 814) to the contracted position. The closed position and the second tissue release position are separated by a second distance ($d_{TR2}$). The first distance ($d_{TR1}$) is less than the second distance ($d_{TR2}$). A ball screw actuator (not shown) is configured to rotate a predetermined number of revolutions corresponding to a desired distance to provide controlled release of first and second portions (T1, T2) of tissue.

FIG. 16I shows a cross-sectional side view of anvil (802) and trocar (804) of stapling head assembly (800) of FIG. 14. FIG. 17I shows a detailed portion of FIG. 16I, with anvil (802) completely separated from trocar (804). As shown, the third tissue release position is separated by a third distance ($d_{TR3}$), which is greater than the first and second distances ($d_{TR1}$, $d_{TR2}$). As shown, in the third tissue release position, the anvil (802) is completely separated from the proximally withdrawn trocar (804) prior to the first and second portions of tissue (T1, T2) being severed and stapled. In other words, this third tissue release position may be used if the user seeks to completely decouple anvil (802) from trocar (804) without severing and stapling of the first and second portions of tissue (T1, T2). This provides an emergency release of the anvil (802) if desired. While not shown, it is also envisioned that the user may utilize the third tissue release position after a partial severing or stapling of the first and second portions of tissue (T1, T2).

The method may also include providing a visual indication (e.g. graphical indicator (500)) on instrument (600) that at least one of: trocar (804) is fully extended, at least one anvil retention feature is in the expanded position, or anvil (802) is spaced from tissue to provide clearance to remove anvil (802) from tissue after firing of instrument (600). As previously described above with reference to FIGS. 10 and 11, handle assembly (610) includes user interface (616) that includes an indicator. For example, indicator may be similar to graphical indicator (500). Graphical indicator (500) may include, for example, fixed linear indicia (502, 504, 506), graphical representations (510, 512) of staples, and/or a checkmark graphic (514), or another suitable graphical indicator. Particularly, indicator may be a light (e.g. an LED light) that changes states in accordance with a condition. Graphical indicator (500) may indicate to the user the condition of when trocar (804) is fully extended. Additionally, graphical indicator (500) may indicate to the user the condition of when both trocar (804) is attached to anvil (802) and trocar (804) is fully extended relative to shaft assembly (630). Graphical indicator (500) may indicate to the user the condition of when anvil (802) is attached to a fully extended trocar (804). Graphical indicator (500) may indicate to the user the condition of when anvil (802) is released enough to remove from tissue after usage. Additionally, graphical indicator (500) may indicate to the user the condition of when anvil (802) is spaced from tissue to remove anvil (802) from tissue after firing of staples (90).

Figure 18:
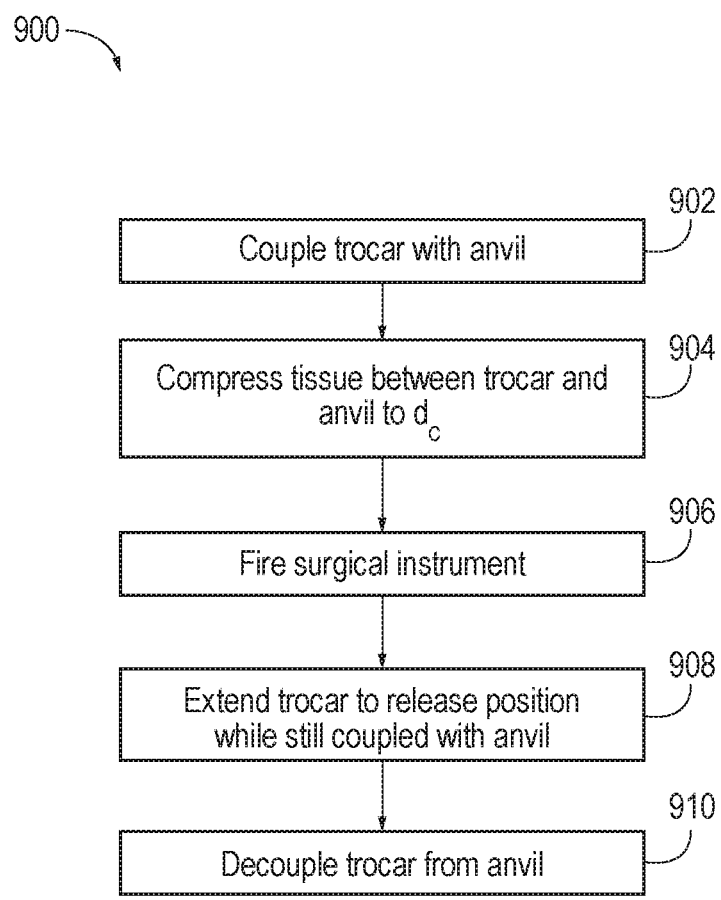
FIG. 18 depicts a diagrammatic view of an exemplary method of operating the circular stapler of FIG. 11 that includes the anvil and the trocar of the stapling head assembly of FIG. 14.

FIG. 18 shows a diagrammatic view of an exemplary method (900) of operating instrument (600) of FIG. 11 that includes of stapling head assembly (800) and anvil (802) of FIG. 14. Step (902) including coupling trocar (804) with anvil (802). This is shown in FIG. 16C and FIG. 17C. Step (904) includes compressing first and second portions (T1, T2) between trocar (804) and anvil (802), such that proximal surface (860) of head (830) of anvil (802) is spaced at a clamped distance ($d_C$) away from deck surface (644), which is less than the pre-compressed distance ($d_{PC}$) as shown in FIG. 16D.

Step (906) includes firing instrument (600). The method also includes moving an anvil (802) of instrument (600) to a predetermined distance away from deck surface (644) after firing at least one annular array of staples (90) of instrument (600). For example, moving anvil (802) to predetermined distance away from deck surface (644) may include moving anvil (802) to predetermined distance away from deck surface (644) using a predetermined number of rotations of a ball screw (not shown). Step (908) includes extending trocar (804) to the first tissue release position shown in FIG. 16F, or a second tissue release position shown in FIG. 16H, while trocar (804) is still coupled with anvil (802). Step (910) includes decoupling trocar (804) from anvil (802) by moving first and second retention features (812, 814) to the contracted position as shown in FIG. 17G, FIG. 17H, and FIG. 17I.

C. Exemplary Alternative Stapling Head Assembly and Anvil

Figure 19B:
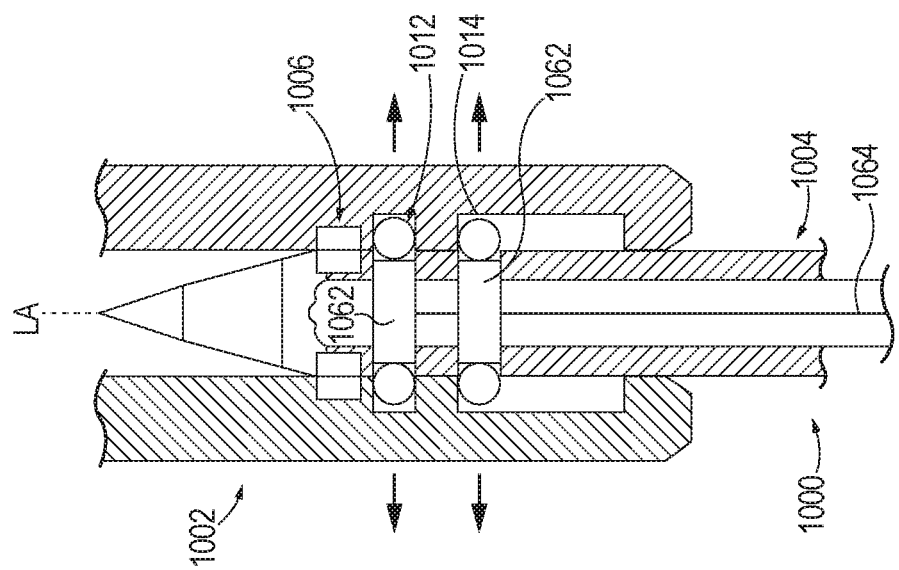
FIG. 19B depicts a cross-sectional side view of anvil and trocar of the stapling head assembly of FIG. 19A, with the trocar is fully inserted into the anvil, the first and second retention features in a contracted position.
Figure 19A:
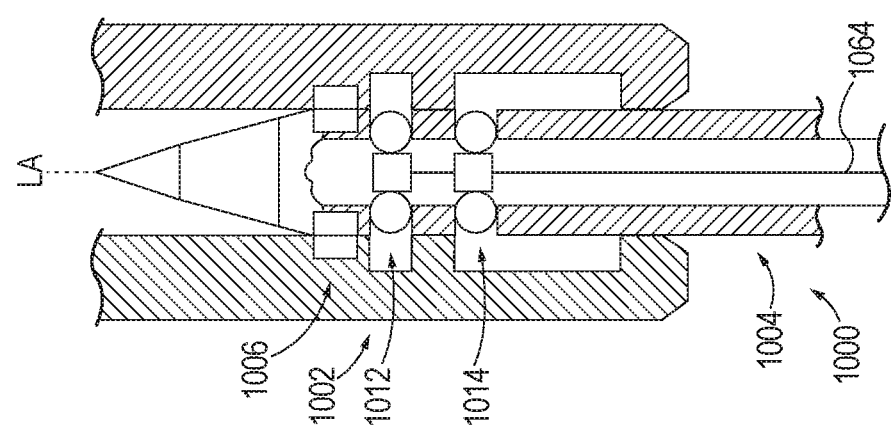
FIG. 19A depicts a cross-sectional side view of another exemplary anvil and trocar of a stapling head assembly, with the trocar fully inserted into the anvil, first and second retention features in a contracted position, and a lockout assembly in a non-locked out configuration similar to FIG. 16B.

FIGS. 19A-19B show cross-sectional side views of an exemplary alternative a stapling head assembly (1000) and an exemplary alternative anvil (1002). Stapling head assembly (1000) is similar to stapling head assembly (800), shown and described above with reference to FIGS. 14-17I. Similarly, anvil (1002) is similar to anvil (802), shown and described above with reference to FIGS. 14-17I. As shown in FIG. 19A, which is similar to FIG. 17B, trocar (1004) is fully inserted into anvil (1002), and first and second retention features (1012, 1014) are in the contracted position. Lockout assembly (1006) is in the non-locked out configuration since first and second retention features (1012, 1014) are in the contracted position.

Unlike FIGS. 17C and 17D, actuating feature (1010) includes electromechanical features (1062) instead of actuating rod (862). Electromechanical features (1062) are configured to outwardly push first and second retention features (1012, 1014) from the contracted position to the expanded position. Electromechanical features (1062) are in electrical communication with control module (672) using a wire (1064). In the expanded position, shaft (1008) of trocar (1004) moves together as a unit with anvil (1002) along longitudinal axis (LA). FIG. 19B shows a cross-sectional side view of anvil (1002) and trocar (1004) of stapling head assembly (1000) of FIG. 19A, with trocar (1004) is fully inserted into anvil (1002), first and second retention features (1012, 1014) in the contracted position.

IV. Exemplary Combinations

The following examples relate to various non-exhaustive ways in which the teachings herein may be combined or applied. The following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument comprising: (a) a body assembly that includes a motor unit; (b) a shaft assembly extending distally from the body assembly; (c) an anvil; and (d) a stapling head assembly positioned at a distal end of the shaft assembly, wherein the stapling head assembly comprises: (i) at least one annular array of staples, (ii) a staple driver configured to drive the at least one annular array of staples against the anvil to deform the staples, and (iii) a trocar comprising: (A) a shaft defining a longitudinal axis, (B) an actuating feature coupled with the motor unit, and (C) at least one coupling feature, wherein the motor unit is configured to actuate the actuating feature to move the at least one coupling feature of the trocar in a transverse direction relative to the longitudinal axis of the shaft between a contracted position and an expanded position, wherein in the contracted position the shaft of the trocar is configured to move along the longitudinal axis relative to the anvil, wherein in the expanded position the shaft of the trocar is configured to move together with the anvil along the longitudinal axis.

Example 2

The surgical instrument of Example 1, wherein the anvil includes at least one interior recess, wherein in the contracted position the at least one coupling feature of the trocar is spaced from the at least one interior recess of the anvil, wherein in the expanded position the at least one coupling feature of the trocar is disposed at least partially within the at least one interior recess of the anvil.

Example 3

The surgical instrument of any of the preceding Examples, wherein the at least one coupling feature includes first and second coupling features that are spaced along the longitudinal axis of the shaft of the trocar, wherein the anvil includes at least first and second interior recesses, wherein in the contracted position the first coupling feature is spaced from the first interior recess and the second coupling feature is spaced from the second interior recess, wherein in the expanded position the first coupling feature is trocar is disposed at least partially within the first interior recess and the second coupling feature is disposed at least partially within the second interior recess.

Example 4

The surgical instrument of any of the preceding Examples, wherein the shaft of the trocar includes a lumen, wherein the actuating feature is configured to move along the longitudinal axis within the lumen to move the at least one coupling feature of the trocar between the contracted position and the expanded position.

Example 5

The surgical instrument of any of the preceding Examples, wherein the actuating feature includes an actuating rod, wherein a distal portion of the actuating rod includes at least one narrow portion having a reduced cross-sectional area, wherein the at least one coupling feature is configured to be disposed within the at least one narrow portion in the contracted position allowing the trocar to move along the longitudinal axis relative to the anvil.

Example 6

The surgical instrument of any of the Examples 1 through 4, wherein the actuating feature includes an electromechanical feature that is configured to outwardly push the at least one coupling feature from the contracted position to the expanded position such that the shaft of the trocar is configured to move together with the anvil along the longitudinal axis.

Example 7

The surgical instrument of any of the preceding Examples, wherein the motor unit comprises first and second independent motors, wherein the first motor is configured to move the actuating feature, wherein the second motor is configured to drive the staple driver.

Example 8

The surgical instrument of any of the preceding Examples, further comprising a lockout assembly that is configured to prevent activation of the actuating feature in response to the anvil not being coupled with the trocar, wherein the lockout assembly is configured to permit activation of the actuating feature in response to coupling of the anvil with the trocar such that the at least one coupling feature is permitted to move to the expanded position.

Example 9

The surgical instrument of Example 8, wherein the lockout assembly comprises an electrical switch, wherein the trocar includes a first electrical contact and the anvil includes a second electrical contact, wherein when the anvil is fully coupled with the trocar the first and second electrical contacts are aligned such that the electrical switch is closed, wherein when the anvil is not fully coupled with the trocar the first and second electrical contacts are not aligned such that the electrical switch is open.

Example 10

The surgical instrument of any of the preceding Examples, wherein in the expanded position, the trocar and anvil are configured to translate as a unit along the longitudinal axis between a closed position, a first tissue release position, and a second tissue release position, wherein a first distance between the closed position and the first tissue release position is less than a second distance between the closed position and the second tissue release position.

Example 11

The surgical instrument of Example 10, wherein at the first tissue release position, the actuating feature is configured to manually or automatically actuate the at least one coupling feature to move the at least one coupling feature to the contracted position.

Example 12

The surgical instrument of any of Examples 10 through 11, wherein at the second tissue release position, the actuating feature is configured to automatically actuate the at least one coupling feature to move the at least one coupling feature to the contracted position.

Example 13

The surgical instrument of any of Examples 1 through 12, wherein the body assembly further includes an indicator that is configured to indicate to a user when the trocar is fully extended.

Example 14

The surgical instrument of any of Examples 1 through 12, wherein the body assembly further includes an indicator that is configured to indicate to a user when both the trocar is attached to the anvil and the trocar is fully extended relative to the body assembly.

Example 15

The surgical instrument of any Examples 1 through 12, wherein the body assembly further includes an indicator that is configured to indicate to a user when the anvil is spaced from tissue to remove the anvil from the tissue after firing of the staples.

Example 16

A surgical instrument comprising: (a) a body assembly that includes a motor unit; (b) a shaft assembly extending distally from the body assembly; (c) an anvil; and (d) a stapling head assembly positioned at a distal end of the shaft assembly, wherein the stapling head assembly comprises: (i) at least one annular array of staples, (ii) a staple driver configured to drive the at least one annular array of staples against the anvil to deform the staples, (iii) a trocar comprising: (A) a shaft defining a longitudinal axis, (B) at least one coupling feature, and (C) an actuating feature coupled with the motor unit, wherein the motor unit is configured to move the actuating feature to move the at least one coupling feature of the trocar between a contracted position and an expanded position, wherein in the contracted position the shaft of the trocar is configured to move along the longitudinal axis relative to the anvil, wherein in the expanded position the shaft of the trocar is configured to move together with the anvil along the longitudinal axis; and (iv) a lockout assembly that is configured to prevent power use by the motor unit to move the actuating feature from the contracted position to the expanded position when the anvil is not fully coupled with the trocar, wherein the lockout assembly is configured to permit the motor unit to move the actuating feature from the contracted position to the expanded position when the anvil is fully coupled with the trocar.

Example 17

The surgical instrument of Example 16, wherein the lockout assembly includes an electrical switch, wherein the electrical switch includes first and second electrical contacts, wherein the trocar includes a first electrical contact and the anvil includes a second electrical contact, wherein when the anvil is fully coupled with the trocar the first and second electrical contacts are configured to be aligned such that the electrical switch is closed, wherein when the anvil is not fully coupled with the trocar the first and second electrical contacts are not configured to be aligned such that the electrical switch is open,

Example 18

The surgical instrument of Example 16, wherein the first and second electrical contacts are configured to detect loading, connection, and retraction of the anvil relative to the shaft of the trocar.

Example 19

A method of operating a surgical instrument, the method comprising: (i) firing the surgical instrument to force at least one annular array of staples through tissue of a patient; and (ii) moving an anvil of the surgical instrument to a predetermined distance away from a deck of an anvil after firing the at least one annular array of staples of the surgical instrument.

Example 20

The method of Example 19, wherein moving the anvil to the predetermined distance away from the deck further comprises moving the anvil to the predetermined distance away from the deck using a predetermined number of rotations of a ball screw.

Example 21

A method for coupling an anvil with a trocar of a surgical instrument, the method comprising: (i) preventing at least one coupling feature of the trocar from engaging the anvil using a lockout assembly when the anvil is not fully coupled with the trocar of the surgical instrument; (ii) determining the anvil is fully inserted into the trocar of the surgical instrument using the lockout assembly; and (iii) moving the at least one coupling feature from a contracted position to an expanded position by activating a motor driven actuating feature after determining the anvil is fully inserted into the trocar.

Example 22

The method of Example 21, further comprising providing a visual indication on the surgical instrument that at least one of the trocar is fully extended, at least one anvil retention feature is in the expanded position, or the anvil is spaced from tissue to provide clearance to remove the anvil from the tissue after firing of the surgical instrument.

Example 23

The method of any of Examples 19 through 20, wherein after moving the at least one anvil retention feature to the expanded position, the method further comprises translating the trocar along a longitudinal axis of the trocar between a closed position and a tissue release position, and at the tissue release position automatically actuating the at least one coupling feature using a control module move the at least one coupling feature to the contracted position.

V. Miscellaneous

It should also be understood that any one or more of the teachings, expressions, embodiments, examples, etc.

described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Furthermore, any one or more of the teachings herein may be combined with any one or more of the teachings disclosed in U.S. patent application Ser. No. 16/574,773, entitled "Method for Calibrating Movements of Actuated Members of Powered Surgical Stapler," filed on Sep. 18, 2019, published as U.S. Pub. No. 2021/0077111 on Mar. 18, 2021; U.S. patent application Ser. No. 16/574,797, entitled "Method for Controlling Cutting Member Actuation for Powered Surgical Stapler," filed on Sep. 18, 2019, published as U.S. Pub. No. 2021/0077112 on Mar. 18, 2021; U.S. patent application Ser. No. 16/574,281, entitled "Method for Controlling End Effector Closure for Powered Surgical Stapler," filed on Sep. 18, 2019, published as U.S. Pub. No. 2021/0077110 on Mar. 18, 2021. The disclosure of each of these U.S. patent applications is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument comprising:
(a) a body assembly that includes a motor unit;
(b) a shaft assembly extending distally from the body assembly;
(c) an anvil; and
(d) a stapling head assembly positioned at a distal end of the shaft assembly, wherein the stapling head assembly comprises:
  (i) at least one annular array of staples,
  (ii) a staple driver configured to drive the at least one annular array of staples against the anvil to deform the staples, and
  (iii) a trocar comprising:
    (A) a shaft defining a longitudinal axis,
    (B) an actuating feature coupled with the motor unit, and
    (C) at least one coupling feature, wherein the motor unit is configured to actuate the actuating feature to move the at least one coupling feature of the trocar in a transverse direction relative to the longitudinal axis of the shaft between a contracted position and an expanded position, wherein in the contracted position the shaft of the trocar is configured to move along the longitudinal axis relative to the anvil, wherein in the expanded position the shaft of the trocar is configured to move together with the anvil along the longitudinal axis.

2. The surgical instrument of claim 1, wherein the anvil includes at least one interior recess, wherein in the contracted position the at least one coupling feature of the trocar is spaced from the at least one interior recess of the anvil, wherein in the expanded position the at least one coupling feature of the trocar is disposed at least partially within the at least one interior recess of the anvil.

3. The surgical instrument of claim 1, wherein the at least one coupling feature includes first and second coupling features that are spaced along the longitudinal axis of the shaft of the trocar, wherein the anvil includes at least first and second interior recesses, wherein in the contracted position the first coupling feature is spaced from the first interior recess and the second coupling feature is spaced from the second interior recess, wherein in the expanded position the first coupling feature is trocar is disposed at least partially within the first interior recess and the second coupling feature is disposed at least partially within the second interior recess.

4. The surgical instrument of claim 1, wherein the shaft of the trocar includes a lumen, wherein the actuating feature is configured to move along the longitudinal axis within the lumen to move the at least one coupling feature of the trocar between the contracted position and the expanded position.

5. The surgical instrument of claim 4, wherein the actuating feature includes an actuating rod, wherein a distal portion of the actuating rod includes at least one narrow portion having a reduced cross-sectional area, wherein the at least one coupling feature is configured to be disposed within the at least one narrow portion in the contracted position allowing the trocar to move along the longitudinal axis relative to the anvil.

6. The surgical instrument of claim 1, wherein the actuating feature includes an electromechanical feature that is configured to outwardly push the at least one coupling feature from the contracted position to the expanded position such that the shaft of the trocar is configured to move together with the anvil along the longitudinal axis.

7. The surgical instrument of claim 1, wherein the motor unit comprises first and second independent motors, wherein the first motor is configured to move the actuating feature, wherein the second motor is configured to drive the staple driver.

8. The surgical instrument of claim 1, further comprising a lockout assembly that is configured to prevent activation of the actuating feature in response to the anvil not being coupled with the trocar, wherein the lockout assembly is configured to permit activation of the actuating feature in response to coupling of the anvil with the trocar such that the at least one coupling feature is permitted to move to the expanded position.

9. The surgical instrument of claim 8, wherein the lockout assembly comprises an electrical switch, wherein the trocar includes a first electrical contact and the anvil includes a second electrical contact, wherein when the anvil is fully coupled with the trocar the first and second electrical contacts are aligned such that the electrical switch is closed, wherein when the anvil is not fully coupled with the trocar the first and second electrical contacts are not aligned such that the electrical switch is open.

10. The surgical instrument of claim 1, wherein in the expanded position, the trocar and anvil are configured to translate as a unit along the longitudinal axis between a closed position, a first tissue release position, and a second tissue release position, wherein a first distance between the closed position and the first tissue release position is less than a second distance between the closed position and the second tissue release position.

11. The surgical instrument of claim 10, wherein at the first tissue release position, the actuating feature is configured to manually or automatically actuate the at least one coupling feature to move the at least one coupling feature to the contracted position.

12. The surgical instrument of claim 10, wherein at the second tissue release position, the actuating feature is configured to automatically actuate the at least one coupling feature to move the at least one coupling feature to the contracted position.

13. The surgical instrument of claim 1, wherein the body assembly further includes an indicator that is configured to indicate to a user when the trocar is fully extended.

14. The surgical instrument of claim 1, wherein the body assembly further includes an indicator that is configured to indicate to a user when both the trocar is attached to the anvil and the trocar is fully extended relative to the body assembly.

15. The surgical instrument of claim 1, wherein the body assembly further includes an indicator that is configured to indicate to a user when the anvil is spaced from tissue to remove the anvil from the tissue after firing of the staples.

16. A surgical instrument comprising:
(a) a body assembly that includes a motor unit;
(b) a shaft assembly extending distally from the body assembly;
(c) an anvil; and
(d) a stapling head assembly positioned at a distal end of the shaft assembly, wherein the stapling head assembly comprises:
(i) at least one annular array of staples,
(ii) a staple driver configured to drive the at least one annular array of staples against the anvil to deform the staples,
(iii) a trocar comprising:
(A) a shaft defining a longitudinal axis,
(B) at least one coupling feature, and
(C) an actuating feature coupled with the motor unit, wherein the motor unit is configured to move the actuating feature to move the at least one coupling feature of the trocar between a contracted position and an expanded position, wherein in the contracted position the shaft of the trocar is configured to move along the longitudinal axis relative to the anvil, wherein in the expanded position the shaft of the trocar is configured to move together with the anvil along the longitudinal axis; and
(iv) a lockout assembly that is configured to prevent power use by the motor unit to move the actuating feature from the contracted position to the expanded position when the anvil is not fully coupled with the trocar, wherein the lockout assembly is configured to permit the motor unit to move the actuating feature from the contracted position to the expanded position when the anvil is fully coupled with the trocar.

17. The surgical instrument of claim 16, wherein the lockout assembly includes an electrical switch, wherein the electrical switch includes first and second electrical contacts, wherein the trocar includes a first electrical contact and the anvil includes a second electrical contact, wherein when the anvil is fully coupled with the trocar the first and second electrical contacts are configured to be aligned such that the electrical switch is closed, wherein when the anvil is not fully coupled with the trocar the first and second electrical contacts are not configured to be aligned such that the electrical switch is open.

18. The surgical instrument of claim 17, wherein the first and second electrical contacts are configured to detect loading, connection, and retraction of the anvil relative to the shaft of the trocar.

* * * * *